United States Patent
Racchini et al.

(10) Patent No.: US 12,318,293 B2
(45) Date of Patent: Jun. 3, 2025

(54) SYSTEM AND METHOD OF STEPPED DEPLOYMENT OF PROSTHETIC HEART VALVE

(71) Applicant: Medtronic, Inc., Minneapolis, MN (US)

(72) Inventors: Joel Racchini, Edina, MN (US); Paul Rothstein, Elk River, MN (US); Jeffrey Sandstrom, Scandia, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 18/609,498

(22) Filed: Mar. 19, 2024

(65) Prior Publication Data

US 2024/0261096 A1    Aug. 8, 2024

Related U.S. Application Data

(63) Continuation of application No. 17/168,903, filed on Feb. 5, 2021, now Pat. No. 11,957,581, which is a (Continued)

(51) Int. Cl.
*A61F 2/24* (2006.01)
*A61F 2/95* (2013.01)

(52) U.S. Cl.
CPC .......... *A61F 2/2436* (2013.01); *A61F 2/2418* (2013.01); *A61F 2/9522* (2020.05); *A61F 2/9524* (2020.05)

(58) Field of Classification Search
CPC ........ A61F 2/24; A61F 2/2418; A61F 2/2427; A61F 2/243; A61F 2/2433; A61F 2/2436; (Continued)

(56) References Cited

U.S. PATENT DOCUMENTS

| 5,035,706 A | 7/1991 | Giantureo et al. |
| 5,445,646 A | 8/1995 | Euteneuer et al. |

(Continued)

FOREIGN PATENT DOCUMENTS

WO    2009/091509    7/2009

OTHER PUBLICATIONS

PCT/US2017/020738, The International Search Report and the Written Opinion of the International Searching Authority, dated Apr. 24, 2017.
(Continued)

*Primary Examiner* — Kankindi Rwego
(74) *Attorney, Agent, or Firm* — Wentsler LLC

(57) ABSTRACT

A system for replacing a heart valve of a patient. The system includes a delivery device and a prosthetic heart valve. The system is configured to be transitionable between a loaded state, a partially deployed state and a deployed state. In the loaded state, the prosthetic heart valve engages a coupling structure and is compressively retained within a primary capsule, which constrains the prosthetic heart valve in a compressed arrangement. In the partially deployed state, the prosthetic heart valve engages the coupling structure and is compressively retained within a secondary capsule, which constrains the prosthetic heart valve to a partially deployed arrangement. The partially deployed arrangement is less compressed than the compressed arrangement and less expanded than a deployed arrangement. In the deployed state, the primary and secondary capsules are retracted from over the prosthetic heart valve, which expands to the deployed arrangement and is released from the coupling structure.

11 Claims, 16 Drawing Sheets

Related U.S. Application Data continuation of application No. 16/167,676, filed on Oct. 23, 2018, now Pat. No. 10,945,840, which is a continuation of application No. 14/231,879, filed on Apr. 1, 2014, now Pat. No. 10,149,758.

(58) Field of Classification Search
CPC .... A61F 2/2439; A61F 2/2463; A61F 2/2466; A61F 2/82; A61F 2/95; A61F 2/954; A61F 2/962; A61F 2/966; A61F 2/97; A61F 2002/9505; A61F 2002/9517; A61F 2002/9522; A61F 2002/9534; A61F 2002/9665
USPC ........................................................ 606/2.11
See application file for complete search history.

(56) References Cited

U.S. PATENT DOCUMENTS

| | | |
|---|---|---|
| 5,683,451 A | 11/1997 | Lenker et al. |
| 5,693,084 A | 12/1997 | Chuter |
| 5,776,186 A | 7/1998 | Uflacker |
| 5,957,949 A | 9/1999 | Leonhardt et al. |
| 5,968,069 A | 10/1999 | Dusbabek et al. |
| 6,113,608 A | 9/2000 | Monroe et al. |
| 6,280,465 B1 | 8/2001 | Cryer |
| 6,517,550 B1 | 2/2003 | Konya et al. |
| 6,733,521 B2 | 5/2004 | Chobotov et al. |
| 6,740,111 B1 | 5/2004 | Lauterjung |
| 6,945,990 B2 | 9/2005 | Greenan |
| 7,033,390 B2 | 4/2006 | Johnson et al. |
| 7,329,275 B2 | 2/2008 | Yee |
| 7,503,929 B2 | 3/2009 | Johnson et al. |
| 7,758,625 B2 | 7/2010 | Wu et al. |
| 7,935,140 B2 | 5/2011 | Griffin |
| 7,993,392 B2 | 8/2011 | Righini et al. |
| 8,052,750 B2 | 11/2011 | Tuval et al. |
| 8,403,981 B2 | 3/2013 | Forster et al. |
| 8,518,098 B2 | 8/2013 | Roeder et al. |
| 9,198,783 B2 | 12/2015 | Douk et al. |
| 9,592,142 B2 | 3/2017 | Dillon et al. |
| 10,149,758 B2 | 12/2018 | Racchini et al. |
| 10,893,938 B2 | 1/2021 | Tran et al. |
| 10,945,840 B2 | 3/2021 | Racchini et al. |
| 2003/0114910 A1 | 6/2003 | Juhani Laakso et al. |
| 2004/0111111 A1 | 6/2004 | Lin |
| 2005/0119722 A1 | 6/2005 | Styrc et al. |
| 2005/0283223 A1 | 12/2005 | Greenan |
| 2006/0074477 A1 | 4/2006 | Berthiaume |
| 2006/0100687 A1 | 5/2006 | Fahey et al. |
| 2006/0265056 A1 | 11/2006 | Nguyen et al. |
| 2007/0239266 A1 | 10/2007 | Birdsall |
| 2007/0239269 A1 | 10/2007 | Dolan et al. |
| 2008/0065011 A1 | 3/2008 | Marchand et al. |
| 2008/0262507 A1* | 10/2008 | Righini ............... A61F 2/2436 623/2.11 |
| 2008/0319526 A1 | 12/2008 | Hill et al. |
| 2009/0062908 A1 | 3/2009 | Bonhoeffer et al. |
| 2009/0281610 A1 | 11/2009 | Parker |
| 2009/0318947 A1 | 12/2009 | Garcia et al. |
| 2010/0100167 A1 | 4/2010 | Bortlein et al. |
| 2010/0168835 A1 | 7/2010 | Dorn |
| 2010/0286768 A1 | 11/2010 | Alkhatib |
| 2011/0015616 A1 | 1/2011 | Straubinger et al. |
| 2011/0040366 A1 | 2/2011 | Goetz et al. |
| 2011/0098805 A1 | 4/2011 | Dwork et al. |
| 2011/0251676 A1 | 10/2011 | Sweeney et al. |
| 2011/0251679 A1 | 10/2011 | Wiemeyer et al. |
| 2011/0251680 A1 | 10/2011 | Tran et al. |
| 2011/0251682 A1 | 10/2011 | Murray, III et al. |
| 2011/0264198 A1 | 10/2011 | Murray, III et al. |
| 2012/0277734 A1 | 11/2012 | Goetz et al. |
| 2013/0013047 A1 | 1/2013 | Ramos et al. |
| 2013/0110223 A1 | 5/2013 | Munsinger et al. |
| 2013/0245752 A1 | 9/2013 | Goetz et al. |
| 2013/0274870 A1* | 10/2013 | Lombardi ............. A61F 2/2427 623/2.11 |
| 2013/0304179 A1 | 11/2013 | Bialas et al. |
| 2013/0338677 A1 | 12/2013 | Schwitzer et al. |
| 2013/0338755 A1 | 12/2013 | Goetz et al. |
| 2014/0222142 A1 | 8/2014 | Kovalsky et al. |
| 2014/0296959 A1 | 10/2014 | Leanna et al. |
| 2014/0330368 A1 | 11/2014 | Gloss et al. |
| 2015/0112430 A1 | 4/2015 | Creaven et al. |
| 2015/0238315 A1 | 8/2015 | Rabito et al. |
| 2015/0297379 A1 | 10/2015 | Green |
| 2016/0270935 A1 | 9/2016 | Rasmussen et al. |
| 2017/0165067 A1 | 6/2017 | Barajas-Torres et al. |

OTHER PUBLICATIONS

U.S. Appl. No. 62/117,013, filed Feb. 17, 2015, Duffy.

* cited by examiner

SYSTEM AND METHOD OF STEPPED DEPLOYMENT OF PROSTHETIC HEART VALVE

CROSS-REFERENCE TO RELATED APPLICATIONS

This application is a continuation of U.S. patent application Ser. No. 17/168,903, filed Feb. 5, 2021, which is a continuation of U.S. patent application Ser. No. 16/167,676, filed Oct. 23, 2018, now U.S. Pat. No. 10,945,840, which is a continuation of U.S. patent application Ser. No. 14/231,879, filed Apr. 1, 2014, now U.S. Pat. No. 10,149,758, the entire contents of each application which are incorporated herein by reference.

BACKGROUND

The present disclosure relates to systems and methods for percutaneous implantation of a heart valve prosthesis. More particular, it relates to delivery systems and methods of stepped deployment of prosthetic heart valves.

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position.

Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced with an implanted prosthetic heart valve. Conventionally, heart valve replacement surgery is an open heart procedure conducted under general anesthesia, during which the heart is stopped and blood flow is controlled by a heart-lung bypass machine.

Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive replacement of cardiac valves. Recently, prosthetic valves supported by stent frame structures that can be delivered percutaneously using a catheter-based delivery system have been developed for heart and venous valve replacement.

With these percutaneous transcatheter (or transluminal) techniques, a valve prosthesis is compacted for delivery via a catheter and then advanced, for example, through an opening in the femoral artery and through the descending aorta to the heart, where the prosthesis is then deployed in the annulus of the valve to be repaired (e.g., the aortic valve annulus).

Percutaneously delivered prosthetic valves may include either self-expandable, balloon-expandable, and/or mechanically-expandable stent frame structures with a valve structure attached or coupled to the interior of the stent frame structure. The prosthetic valve may be reduced in diameter, by crimping onto a balloon catheter or by being contained within a sheath component of a delivery catheter, and advanced through the venous or arterial vasculature.

Once the prosthetic valve is positioned at the treatment site, for instance within an incompetent native valve, the stent frame structure may be expanded to hold the prosthetic valve firmly in place. One example of a stented prosthetic valve is disclosed in U.S. Pat. No. 5,957,949 to Leonhardt et al., which is incorporated by reference herein in its entirety.

Although transcatheter techniques have attained widespread acceptance with respect to the delivery of conventional stents to restore vessel patency, only mixed results have been realized with percutaneous delivery of a relatively more complex prosthetic heart valve.

Various types and configurations of prosthetic heart valves are available, and continue to be refined. The actual shape and configuration of any particular prosthetic heart valve is dependent to some extent upon native shape and size of the valve being repaired (i.e., mitral valve, tricuspid valve, aortic valve, or pulmonary valve). In general, prosthetic heart valve designs attempt to replicate the functions of the valve being replaced and thus may include a valve structure comprising one or more leaflet-like structures.

With a bioprosthesis construction, the replacement valve may include a valved vein segment that is mounted in some manner within an expandable stent frame to make a valved stent (or "stented prosthetic heart valve"). For many percutaneous delivery and implantation systems, the self-expanding valved stent is crimped down to a desired size and held in that compressed state within an outer sheath, for example. Retracting the sheath from the valved stent allows the stent to self-expand to a larger diameter, such as when the valved stent is in a desired position within a patient.

In other percutaneous implantation systems, the valved stent can be initially provided in an expanded or uncrimped condition, then crimped or compressed on a balloon portion of a catheter until it is as close to the diameter of the catheter as possible. Once delivered to the implantation site, the balloon is inflated to deploy the so-configured prosthesis. With either of these types of percutaneous stent delivery systems, conventional sewing of the prosthetic heart valve to the patient's native tissue is typically not necessary.

It is imperative that the stented prosthetic heart valve be accurately positioned relative to the native valve immediately prior to deployment from the catheter as successful implantation requires the transcatheter prosthetic heart valve intimately lodge and seal against the native tissue. If the prosthesis is incorrectly positioned relative to the native tissue, serious complications can result as the deployed device can leak and may even dislodge from the implantation site.

In an effort to enhance the accuracy of the prosthetic heart valve placement, imaging technology has been utilized to assist a clinician in better evaluating the position of the transcatheter prosthetic heart valve immediately prior to deployment and implantation.

In light of the above, although there have been advances in percutaneous valve replacement techniques and devices, there is a continued desire to provide different delivery systems for delivering cardiac replacement valves, and in particular, expandable stented prosthetic heart valves, to an implantation site in a minimally invasive and percutaneous manner.

SUMMARY

An embodiment of the invention is directed to a system for replacing a heart valve of a patient. The system includes a delivery device and a prosthetic heart valve. The delivery device has an inner shaft assembly, a primary capsule and a secondary capsule.

The inner shaft assembly includes an intermediate portion providing a coupling structure. The primary capsule is slidably disposed over the inner shaft assembly. The secondary capsule is slidably disposed over the inner shaft assembly.

The prosthetic heart valve has a stent frame and a valve structure attached or coupled to the stent frame. The prosthetic heart valve is expandable (e.g., self-expandable). The system is configured to be transitionable between a loaded compressed state, a partially deployed, partially compressed, or partially expanded state and a deployed or expanded state. In the loaded state, the prosthetic heart valve engages the coupling structure and is compressively retained within the primary capsule. The primary capsule constrains the prosthetic heart valve in a compressed arrangement.

In the partially deployed state, the prosthetic heart valve engages the coupling structure and is compressively retained within the secondary capsule. The partially deployed state includes the primary capsule at least partially retracted from over the prosthetic heart valve and the secondary capsule at least partially constraining the prosthetic heart valve to a partially deployed arrangement. The partially deployed arrangement is less compressed than the loaded arrangement and less expanded than the deployed arrangement.

In the deployed state, the primary and secondary capsules are retracted from over the prosthetic heart valve and the prosthetic heart valve is expanded to the deployed arrangement and released from the coupling structure.

Another embodiment of the invention is directed to a method of deploying a stented prosthetic heart valve at an implantation site. A system is received in a loaded state. The system includes a delivery device loaded with a prosthetic heart valve. The prosthetic heart valve has a stent frame to which a valve structure is attached. The delivery device includes an inner shaft assembly, a primary capsule and a secondary capsule. The loaded state includes the prosthetic heart valve coupled to the inner shaft assembly and compressibly retained within the primary capsule in a compressed arrangement.

The prosthetic heart valve is delivered to a location proximate the implantation site though a bodily lumen of the patient with the system in the loaded state. The system is transitioned to a partially deployed arrangement where the prosthetic heart valve is coupled to the inner shaft assembly and compressibly retained in the secondary capsule in the partially deployed arrangement that is less compressed and more expanded than the compressed or loaded arrangement and more compressed and less expanded than the expanded or deployed arrangement. The partially deployed arrangement includes the primary capsule retracted from over the prosthetic heart valve.

With the system in the partially deployed arrangement, the prosthetic heart valve is arranged and positioned within the implantation site. The system is transitioned to the expanded or deployed arrangement in which the secondary capsule is retracted from over the prosthetic heart valve and the prosthetic heart valve is then released from the delivery device.

DETAILED DESCRIPTION

Figure 1A:
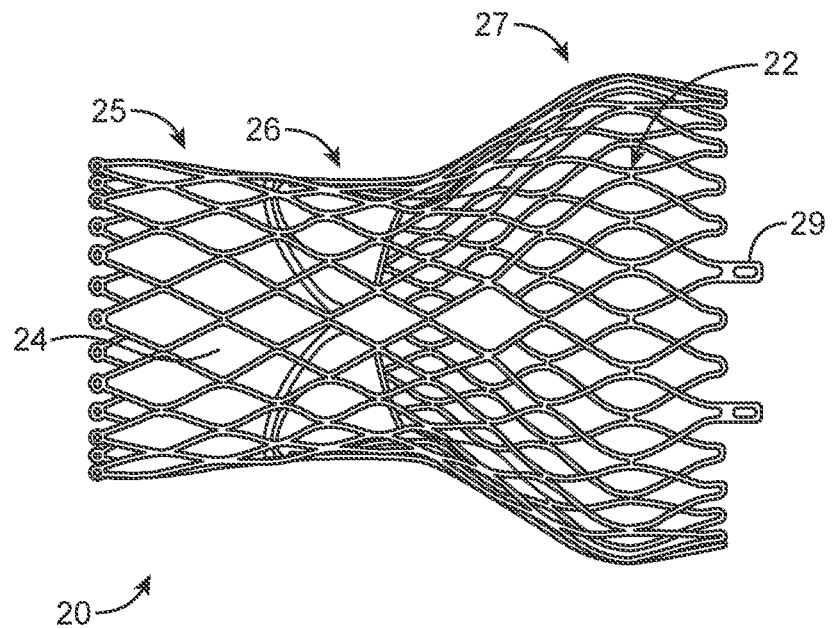
FIG. 1A is a side view of a prosthetic heart valve in an expanded arrangement and useful with systems and methods of the present disclosure.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to an implanted valve prosthesis, the terms "distal", "outlet", and "outflow" are understood to mean downstream to the direction of blood flow, and the terms "proximal", "inlet", or "inflow" are understood to mean upstream to the direction of blood flow. In addition, as used herein, the terms "outward" or "outwardly" refer to a position radially away from a longitudinal axis of a frame of the valve prosthesis and the terms "inward" or "inwardly" refer to a position radially toward a longitudinal axis of the frame of the valve prosthesis. As well the terms "backward" or "backwardly" refer to the relative transition from a downstream position to an upstream position and the terms "forward" or "forwardly" refer to the relative transition from an upstream position to a downstream position.

The invention is directed to a system and method for deploying a prosthetic heart valve 20 that enables the prosthetic heart valve 20 to be partially deployed to evaluate whether the prosthetic heart valve 20 has been accurately positioned with respect to a native valve. The invention thereby improves the ability to accurately position the prosthetic heart valve 20.

As referred to herein, the prosthetic heart valve 20 as used in accordance with the various devices and methods may include a wide variety of different configurations, such as a bioprosthetic heart valve structure having one or more tissue leaflets or a synthetic heart valve structure having one or more polymeric, metallic, or tissue-engineered leaflets, and can be specifically configured for replacing any heart valve.

In accordance with embodiments hereof, one or more portions of the valve structure, body, component, or member, and valve leaflets thereof, can be formed, for example, from one or more biocompatible synthetic materials, synthetic polymers, autograft tissue, homograft tissue, xenograft tissue, or one or more other suitable materials. In some embodiments, one or more portions of the valve structure and valve leaflets thereof can be formed, for example, from bovine, porcine, equine, ovine, and/or other suitable animal tissues.

In accordance with embodiments hereof, one or more portions of the valve structure and valve leaflets thereof may be made of or formed from a natural material obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. In accordance with other embodiments hereof, synthetic materials suitable for use as valve structure components and valve leaflets thereof include DACRON® polyester commercially available from Invista North America S.A.R.L. of Wilmington, DE, other cloth materials, nylon blends, polymeric materials, and vacuum deposition nitinol fabricated materials. In an embodiment, one or more portions of the valve structure and valve leaflets thereof can be made of an ultra-high molecular weight polyethylene material commercially available under the trade designation DYNEEMA from Royal DSM of the Netherlands.

With certain leaflet materials, it may be desirable to coat one or both sides of the leaflet with a material that will prevent or minimize overgrowth. It is further desirable that the leaflet material is durable and not subject to stretching, deforming, or fatigue. In accordance with other embodiments hereof, the valve structure can comprise one or more valve leaflets. For example, the valve structure can be in the form of a tri-leaflet bovine pericardium valve, a bi-leaflet valve, or another suitable valve. In accordance with other embodiments hereof, the valve structure can comprise three leaflets that are fastened together at enlarged lateral end regions to form commissural joints, with the unattached edges forming coaptation edges of the valve structure. In accordance with other embodiments hereof, the prosthetic valve leaflets can be fastened to a skirt of a graft material, which in turn can be attached or coupled to the stent frame.

As referred to herein, the prosthetic heart valve 20 as used in accordance with the devices and methods of the present disclosure can be generally used for replacement of a native aortic, mitral, pulmonic, or tricuspid valve, for use as a venous valve, or to replace a failed bioprosthesis, such as in the area of an aortic valve or mitral valve, for example.

Figure 1B:
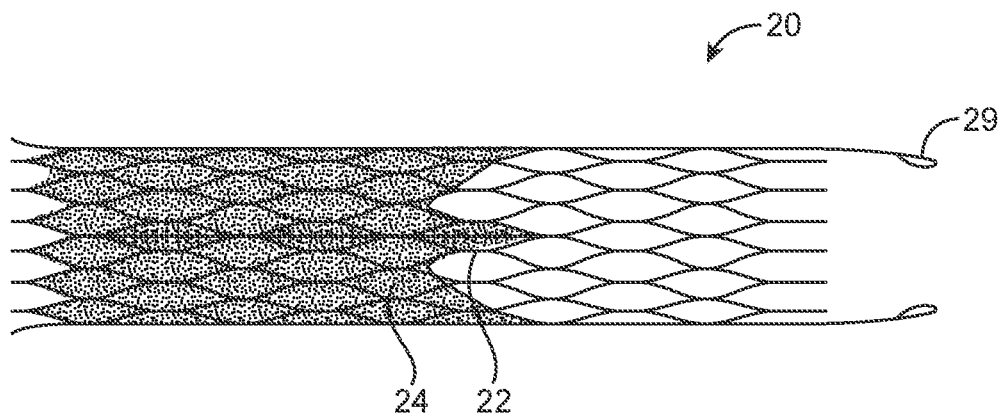
FIG. 1B is a side view of the prosthetic heart valve of FIG. 1A in a compressed arrangement

In general terms, the prosthetic heart valves 20 of the present disclosure may comprise a stent or stent frame 22 maintaining a valve structure (tissue or synthetic) 24 as illustrated in FIGS. 1A and 1B. Stent frame 22 includes an inlet portion 25, a central portion 26, and an outlet portion 27, The stent frame 22 has an expanded arrangement (FIG. 1A) for maintaining the prosthetic heart valve 20 in a desired implant location and a collapsed or compressed arrangement (FIG. 1B) for loading within the delivery system 10.

Figure 2:
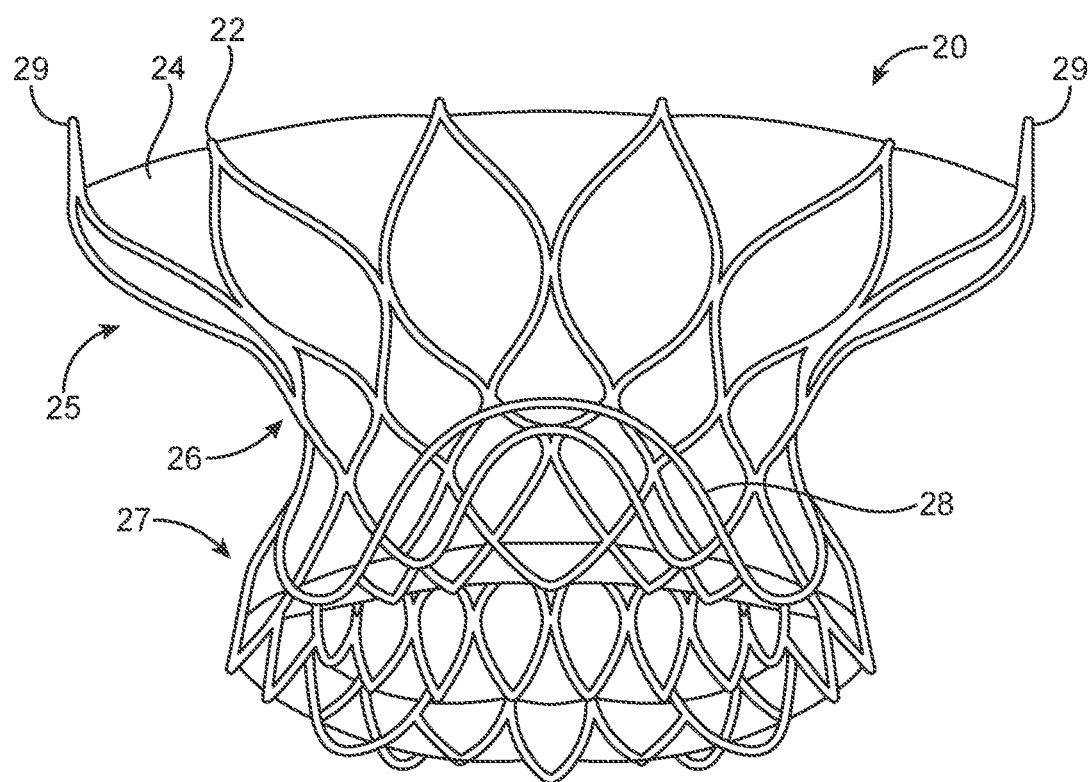
FIG. 2 is a side view of a prosthetic heart valve in an expanded arrangement and useful with systems and methods of the present disclosure.

FIG. 2 is a front or side view of a valve prosthesis 20 in accordance with an embodiment hereof. Valve prosthesis 20 includes a valve structure 24 supported within a stent frame 22. Stent frame 22 includes an inlet portion 25, an hourglass-shaped central or valve-retaining tubular portion 26, an outlet portion 27, and support arms 28. Support arms 28 maybe configured to capture leaflets during delivery of valve prosthesis 20. Central portion 26 maybe configured to pinch a muscular ridge of the native annulus when implanted therein. The reduced-waist region of the hourglass shape or profile of stent frame 22 maybe located on or defined within central portion 26 around the entire circumference of stent frame 22. Stent frame 22 may also provide axial fixation by creating tensioning of the chordae tendinae (CT).

In certain embodiments, the stent frame 22 is constructed to self-deploy or self-expand when released from the delivery system 10. For example, the stented prosthetic heart valve useful with the present disclosure can be a prosthetic valve sold under the trade name CoreValve® available from Medtronic, Inc. Other non-limiting examples of transcatheter heart valve prostheses useful with systems and methods of the present disclosure are described in U.S. Pat. No. 8,052,750, U.S. patent Publication Nos. 2006/0265056; 2007/0239266; and 2007/0239269, and U.S. patent application Ser. No. 14/175,100, the teachings of each of which are incorporated herein by reference.

The stents or stent frames 22 are support structures that may include a number of struts and/or wire portions arranged relative to each other to provide a desired compressibility and strength to the prosthetic heart valve 20. In general terms, the stents or stent frames 22 of the present disclosure are generally tubular support structures having an internal area in which valve structure leaflets are secured.

Leaflets in the valve structure 24 can be formed from a variety of materials as described above, such as autologous tissue, xenograph material, or synthetics as are known in the art. The leaflets may be provided as a homogenous, biological valve structure, such as porcine, bovine or equine valves. Alternatively, the leaflets can be provided independent of one another (e.g., leaflets made from bovine or equine pericardial tissue) and subsequently assembled to the support structure of the stent frame.

In another alternative, the stent frame 22 and the valve structure 24 can be fabricated at the same time, such as may be accomplished using high-strength nano-manufactured NiTi films produced at Advance BioProsthetic Surfaces (ABPS), for example.

The stent frame support structures are generally configured to accommodate a valve structure comprising two or three leaflets. However, replacement prosthetic heart valve 20 of the types described herein can incorporate a valve structure comprising one or more leaflets.

Some embodiments of the stent frames 22 can be a series of wires, wire segments and/or struts arranged such that they are capable of self-transitioning from a collapsed arrangement to a radially expanded arrangement. In constructions, a one or more portions of the stent frame support structure 22 can be formed of one or more metals and/or other materials. The wires and/or struts may be arranged in such a way that the stent frame support structure allows for folding or compressing or crimping to the compressed arrangement in which its internal diameter is smaller than its internal diameter when in the expanded arrangement. In some embodiments, the valve prosthesis comprising a stent frame support structure with an attached or coupled valve structure can be mounted in a collapsed or compressed configuration or arrangement into or onto a delivery system.

The stent frame support structures are configured so that they can be changed to their expanded arrangement when desired, such as by the relative movement of one or more sheaths relative to a length of the stent frame. The wires and/or struts of the stent frame support structures in embodiments of the present disclosure may be formed from a shape memory material such as a nickel titanium alloy (e.g., Nitinol™). With this material, the support structure may be self-expandable from a compressed arrangement to an expanded arrangement, such as by the application of heat, energy, and the like, or by the removal of external forces (e.g., compressive forces).

The stent frame support structure may be configured to be compressed and re-expanded multiple times without damaging the structure of the stent frame. In some embodiments, the stent frame support structure may be laser-cut from a single piece of material or may be assembled from a number of different materials and/or components.

In order to transform between an initial compressed configuration and a deployed configuration, the stent frame support structure in accordance with embodiments described herein may be formed from a self-expanding material that has a mechanical memory to return to the deployed configuration. Accordingly in accordance with embodiments hereof, stent frames may be made from stainless steel, a pseudo-elastic metal such as a nickel titanium alloy or nitinol, or a so-called super alloy, which may have a base metal of nickel, cobalt, chromium, or other metal. Mechanical memory may be imparted to a tubular structure that may form stent frames by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. In accordance with other embodiments hereof, a stent frame of the valve prosthesis can be formed entirely or in part by a biocompatible or biodegradable material. In accordance with other embodiments hereof, one or more portions of a stent frame of the valve prosthesis may be self-expandable, balloon expandable, and/or mechanically-expandable.

One or more valve prosthesis embodiments disclosed herein may comprise a single support arm, a plurality of support arms, support arms with inner and outer support arm members, variations of structures thereof, and/or one or more pairs of support arms having various structures and attachment points for providing various functions when implanted. It should be understood that the illustrated embodiments hereof are not limited to the number or configuration of support arms illustrated in each figure and that one or more support arms, one or more pairs of support arms and/or the various structures therefore may be substituted across the various embodiments disclosed herein without departing from the scope hereof.

In one or more embodiments, valve prosthesis may comprise one or more support arms for engaging one or more native valve leaflets. In one or more embodiments, valve prosthesis may comprise one or more support arms for engaging one or more native chordae. In one or more embodiments, valve prosthesis may comprise one or more support arms for engaging one or more native valve commissures. In one or more embodiments, valve prosthesis may comprise one or more support arms for engaging a native valve annulus. In one or more embodiments, valve prosthesis may comprise one or more support arms for engaging one or more native valve tissues or structures. For example, one or more support arms may engage or interact with valve leaflets, chordae, commissures and/or annulus. In one or more embodiments, valve prosthesis may comprise one or more support arms for engaging one or more heart tissues or structures. In one or more embodiments, valve prosthesis may comprise one or more support arms for engaging the pulmonary artery. In one or more embodiments, valve prosthesis may comprise one or more support arms for engaging the aorta.

In one or more embodiments, one or more support arms may be coupled or connected to a central portion, an inflow portion and/or an outflow portion of valve prosthesis. In one or more embodiments, valve prosthesis may comprise one or more support arms that may apply one or more forces such as a radial force, an axial force, a lateral force, an inward force, an outward force, an upstream force, and/or a downstream force to one or more valve structures, valve tissues, heart structures and/or heart tissues. In some embodiments, one or more support arms, as described herein, may be considerably longer, shorter, wider, or narrower than shown. In some embodiments, one or more support arms, as described herein, may be narrower at the base, bottom or proximal end portion where the support arms couple to the inflow portion, central portion and/or the outflow portion of the valve prosthesis and wider at the top or distal end portion of the support arm. In some embodiments, one or more support arms, as described herein, may be wider at the base, bottom, or proximal end portion where the support arms couple to the inflow portion, central portion and/or the outflow portion of the valve prosthesis and narrower at the top or distal end portion of the support arm. In some embodiments, one or more support arms, as described herein, may be configured to be a shape and size that can provide a positioning function, valve leaflet capturing function, a stabilization function, an anti-migration function, and/or an anchoring function for valve prosthesis in accordance herewith when the prosthesis is deployed at a native valve site. In some embodiments, one or more support arms, as described herein, may interact, engage, capture, clamp, push against one or more native tissues or structures such as valve leaflets, chordae, annulus, ventricle, and/or atrium. In some embodiments, one or more support arms, as described herein, may comprise a first portion that extends in a forward direction and a second portion that extends in a backward direction. In some embodiments, one or more support arms, as described herein, may comprise a first portion that extends in a backward direction and a second portion that extends in a forward direction. In some embodiments, one or more support arms, as described herein, may comprise one or more portions that may extend horizontally, longitudinally, axially, circumferentially, inward, outward, forward, and/or backward. In some embodiments, one or more support arms, as described herein, may comprise more than one configuration. For example, one or more embodiments of one or more support arms, as described herein, may extend in first direction in a delivery, compressed, and/or collapsed configuration and in a second direction in a deployed or expanded configuration. In one example, a first or delivery direction may be a forward direction and a second or deployed direction may be a backward direction. In another example, a first or delivery direction may be a backward direction and a second or deployed direction may be a forward direction. In one or more embodiments, one or more support arms, as described herein, may comprise a first shape in a delivery configuration and a second shape in a deployed configuration. For example, a first or delivery shape may be a straight shape and a second or deployed shape may be a curved shape.

In some embodiments, one or more support arms, as described herein, may comprise one or more portions that comprise one or more spiral shapes, s-shapes, c-shapes, u-shapes, v-shapes, loop shapes, tine shapes, and/or prong shapes. In some embodiments, one or more support arms, as described herein, may comprise a curved, rounded, and/or flared distal end portion. In some embodiments, one or more support arms, as described herein, may be connected, coupled, attached, and/or extend from one or more locations positioned on the inflow portion, the central portion and/or the outflow portion of the valve prosthesis. For example, in some embodiments, one or more support arms, as described herein, may be connected, coupled, attached, and/or extend from one or more locations positioned on the inflow portion, the central portion and/or the outflow portion of the valve prosthesis stent frame support structure. In some embodiments, one or more support arms, as described herein, may comprise at least a portion that may comprise at least one free end not attached or coupled to the stent frame of the valve prosthesis. In one or more embodiments, one or more support arms and/or one or more of components of a support arm may comprise one or more fixation elements or members such as anchors, barbs, prongs, clips, grommets, sutures, and/or screws. In one or more embodiments, one or more support arms and/or one or more of components of a support arm may comprise, for example, one or more active and/or passive fixation elements or members.

In one or more embodiments, valve prosthesis may comprise an inflow portion, a central portion, and an outflow portion. In one or more embodiments, the valve prosthesis may comprise a single unitary structure or the valve prosthesis may comprise one or more components or portions coupled or connected together. In one or more embodiments, the valve prosthesis may comprise a central portion comprising a valve body, member, or component. In one or more embodiments, the valve body, structure, member, or component may comprise one or more valve leaflets. In one or more embodiments in accordance herewith, the valve leaflets of the valve body, structure, member, or component are attached to an upstream end of the central portion to extend into an inflow portion of the frame, such that the valve body, structure, member, or component is not solely located on or within the outflow portion of the frame. In one or more embodiments, valve member and/or one or more of its components may comprise one or more materials, as described herein.

In one or more embodiments, the central portion of valve prosthesis and/or one or more of its components may comprise one or more longitudinal or cross-sectional shapes, such as a geometric shape, a non-geometric shape, a tubular shape, a cylindrical shape, a circular shape, an elliptical shape, an oval shape, a triangular shape, a rectangular shape, a hexagonal shape, a square shape, an hourglass shape, a polygonal shape, a funnel shape, a nozzle shape, a D-shape, a saddle shape, a planar shape, a non-planar shape, a simple geometric shape, and/or a complex geometric shape. In one or more embodiments, the central portion and/or one or more of its components may comprise one or more fixation elements or members such as anchors, barbs, clips, prongs, grommets, sutures, and/or screws. In one or more embodiments, the central portion and/or one or more of its components may comprise a frame, a framework, or stent-like structure, as described herein. In one or more embodiments, the outflow portion and/or one or more of its components may comprise, be covered with, be coated with, or be attached or coupled to one or more materials, as described herein. In one or more embodiments, the central portion and/or one or more of its components may comprise one or more support arms, components, or members as described herein. In one or more embodiments, one or more support arms may comprise one or more cantilever components or portions. In one or more embodiments, the central portion and/or one or more of its components, such as one or more support arms, may be designed to engage and/or push against the native valve annulus. In one or more embodiments, the central portion and/or one or more of its components, such as one or more support arms, may be designed to engage, capture, clamp, hold, and/or trap one or more native valve leaflets. In one or more embodiments, the central portion and/or one or more of its components, such as one or more support arms, may be designed to engage, capture, clamp, hold, and/or trap one or more native chordae. In one or more embodiments, one or more support arms may create or exert a tension force to native chordae. In one or more embodiments, the central portion and/or one or more of its components, such as one or more support arms, may be designed to engage and/or push against one or more native valve commissures.

In one or more embodiments, valve prosthesis may comprise an inflow, inlet, upstream or proximal portion connected, coupled, positioned and/or located at a proximal end or proximal end portion of the central portion of the valve prosthesis. In one or more embodiments, the inflow portion and/or one or more of its components may contact, engage, fixate, capture, clamp, pierce, hold, position and/or seal the valve prosthesis to one or more heart structures and/or tissues such as atrial tissue, ventricle tissue, valve tissue, annulus tissue, the floor of an atrium, and/or the floor of a ventricle. For example, the inflow portion and/or one or more of its components may engage atrial tissue if the valve prosthesis is positioned in a native mitral valve whereas the inflow portion and/or one or more of its components may engage ventricle tissue if the valve prosthesis is positioned in a native aortic valve. In one or more embodiments, the inflow portion and/or one or more of its components may exert one or more forces, for example, radial and/or axial forces, to one or more heart structures and/or heart tissues. In one or more embodiments, the inflow portion and/or one or more of its components may comprise one or more fixation elements or members such as anchors, barbs, clips, prongs, grommets, sutures, and/or screws. In one or more embodiments, the inflow portion and/or one or more of its components may comprise one or more longitudinal or cross-sectional shapes, such as a geometric shape, a non-geometric shape, a tubular shape, a cylindrical shape, a circular shape, an elliptical shape, an oval shape, a triangular shape, a rectangular shape, a hexagonal shape, a square shape, a polygonal shape, a funnel shape, a nozzle shape, a D-shape, an S-shape, a saddle shape, a simple geometric shape, and/or a complex geometric shape. In one or more embodiments, the inflow portion and/or one or more of its components may be designed to deform to the shape of the native anatomy when the valve prosthesis is implanted. For example, the inflow portion may deform from a pre-delivery circular shape to a post-delivery D-shape following the delivery of the valve prosthesis to a native mitral valve. In one or more embodiments, the inflow portion and/or one or more of its components may comprise a frame, a framework, or stent-like structure, as described herein. In one or more embodiments, the inflow portion and/or one or more of its components may comprise, be covered with, be coated with, or be attached or coupled to one or more materials, as described herein. In one or more embodiments, the inflow portion and/or one or more of its components may comprise one or more support arms, components, or members as described herein. In one or more embodiments, one or more support arms may comprise one or more cantilever components or portions. In one or more embodiments, the inflow portion and/or one or more of its components, such as one or more support arms, may be designed to engage and/or push against the native valve annulus. In one or more embodiments, the inflow portion and/or one or more of its components, such as one or more support arms, may be designed to engage, capture, clamp, hold, and/or trap one or more native valve leaflets. In one or more embodiments, the inflow portion and/or one or more of its components, such as one or more support arms, may be designed to engage, capture, clamp, hold, and/or trap one or more native chordae. In one or more embodiments, one or more support arms may create or exert a tension force to native chordae. In one or more embodiments, the inflow portion and/or one or more of its components, such as one or more support arms, may be designed to engage and/or push against one or more native valve commissures.

In one or more embodiments, valve prosthesis may comprise an outflow, outlet, downstream, or distal portion connected, coupled, positioned and/or located at a distal end or distal end portion of the central portion of the valve prosthesis. In one or more embodiments, the outflow portion and/or one or more of its components may contact, engage, fixate, capture, clamp, pierce, hold, position and/or seal the valve prosthesis to one or more heart structures and/or tissues such as atrial tissue, ventricle tissue, valve tissue, valve leaflet tissue, annulus tissue and/or chordae tissue. For example, the outflow portion and/or one or more of its components may engage leaflet tissue, chordae tissue and/or ventricle tissue if the valve prosthesis is positioned in a native mitral valve whereas the outflow portion and/or one or more of its components may engage leaflet tissue and/or aortic tissue if the valve prosthesis is positioned in a native aortic valve. In one or more embodiments, the outflow portion and/or one or more of its components may exert one or more forces, for example, radial and/or axial forces, to one or more heart structures and/or heart tissues. In one or more embodiments, the outflow portion and/or one or more of its components may comprise one or more fixation elements or members such as anchors, barbs, prongs, clips, grommets, sutures, and/or screws. In one or more embodiments, the outflow portion and/or one or more of its components may comprise one or more longitudinal or cross-sectional shapes, such as a geometric shape, a non-geometric shape, a tubular shape, a cylindrical shape, a circular shape, an elliptical shape, an oval shape, a triangular shape, a rectangular shape, a hexagonal shape, a square shape, a polygonal shape, a funnel shape, a nozzle shape, a D-shape, an S-shape, a saddle shape, a simple geometric shape, and/or a complex geometric shape. In one or more embodiments, the outflow portion and/or one or more of its components may be designed to deform to the shape of the native anatomy when the valve prosthesis is implanted. For example, the outflow portion may deform from a pre-delivery circular shape to a post-delivery D-shape following the delivery of the valve prosthesis to a native mitral valve. In one or more embodiments, the outflow portion and/or one or more of its components may comprise a frame, a framework, or stent-like structure, as described herein. In one or more embodiments, the outflow portion and/or one or more of its components may comprise, be covered with, be coated with, or be attached or coupled to one or more materials, as described herein. In one or more embodiments, the outflow portion and/or one or more of its components may comprise one or more support arms, components, or members as described herein. In one or more embodiments, the outflow portion and/or one or more of its components, such as one or more support arms, may be designed to engage, capture, clamp, hold, and/or trap one or more native valve leaflets. In one or more embodiments, the outflow portion and/or one or more of its components, such as one or more support arms, may be designed to engage, capture, clamp, hold, and/or trap one or more native chordae. In one or more embodiments, one or more support arms may create or exert a tension force to native chordae. In one or more embodiments, the outflow portion and/or one or more of its components, such as one or more support arms, may be designed to engage and/or push against one or more native valve commissures. In one or more embodiments, the outflow portion and/or one or more of its components, such as one or more support arms, may be designed to engage and/or push against the native valve annulus. In one or more embodiments, one or more support arms may comprise one or more cantilever components or portions.

In one or more embodiments, valve prosthesis and/or one or more of its components or portions may comprise, be covered with, be coated with, or be attached or coupled to one or more biocompatible materials or biomaterials, for example, titanium, titanium alloys, Nitinol, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers or plastics such as polyamides, polycarbonates, polyethers, polyesters, polyolefins including polyethylenes or polypropylenes, polystyrenes, polyurethanes, polyvinylchlorides, polyvinylpyrrolidones, silicone elastomers, fluoropolymers, polyacrylates, polyisoprenes, polytetrafluoroethylenes, polyethylene terephthalates, fabrics such as woven fabrics, nonwoven fabrics, porous fabrics, semi-porous fabrics, nonporous fabrics, Dacron fabrics, polytetrafluoroethylene (PTFE) fabrics, polyethylene terephthalate (PET) fabrics, materials that promote tissue ingrowth, rubber, minerals, ceramics, hydroxapatite, epoxies, human or animal protein or tissue such as collagen, laminin, elastin or fibrin, organic materials such as cellulose, or compressed carbon, and/or other materials such as glass, and the like. Materials that are not considered biocompatible may be modified to become biocompatible by a number of methods well known in the art. For example, coating a material with a biocompatible coating may enhance the biocompatibility of that material. Biocompatible materials or biomaterials are usually designed and constructed to be placed in or onto tissue of a patient's body or to contact fluid of a patient's body. Ideally, a biocompatible material or biomaterial will not induce undesirable reactions in the body such as blood clotting, tumor formation, allergic reaction, foreign body reaction (rejection) or inflammatory reaction; will have the physical properties such as strength, elasticity, permeability, and flexibility required to function for the intended purpose; may be purified, fabricated and sterilized easily; will substantially maintain its physical properties and function during the time that it remains in contact with tissues or fluids of the body.

In one or more embodiments, valve prosthesis and/or one or more of its components or portions may comprise and/or be coupled or attached to one or more graft materials. In accordance with embodiments hereof, the graft material or portions thereof may be a low-porosity woven fabric, such as polyester, DACRON® polyester, or polytetrafluoroethylene (PTFE), which creates a one-way fluid passage when attached to the stent frame of the valve prosthesis. In an embodiment, the graft material or portions thereof may be a looser knit or woven fabric, such as a polyester or PTFE knit, which can be utilized when it is desired to provide a medium for tissue ingrowth and the ability for the fabric to stretch to conform to a curved surface. In another embodiment, polyester velour fabrics may alternatively be used for the graft material or portions thereof, such as when it is desired to provide a medium for tissue ingrowth on one side and a smooth surface on the other side. These and other appropriate cardiovascular fabrics are commercially available from Bard Peripheral Vascular, Inc. of Tempe, Arizona, for example. In another embodiment, the graft material or portions thereof may be a natural material, such as pericardium or another membranous tissue.

In one or more embodiments, valve prosthesis and/or one or more of its components or portions may comprise, be coated with, be covered with, be constrained by, or be attached or coupled to a shape memory material, a bioresorbable material, and/or a biodegradable material, such as a natural or synthetic biodegradable polymer, non-limiting examples of which include polysaccharides such as alginate, dextran, cellulose, collagen, and chemical derivatives thereof, proteins such as albumin, and copolymer blends thereof, alone or in combination with synthetic polymers, polyhydroxy acids, such as polylactides, polyglycolides and copolymers thereof, poly(ethylene terephthalate), poly(hydroxybutyric acid); poly(hydroxyvaleric acid), poly[lactide-co-(E-caprolactone)]; poly[glycolide-co-(E-caprolactone)], polycarbonates, poly(pseudo amino acids); poly(amino acids); poly(hydroxyalkanoate)s, polyanhydrides; polyortho esters, and blends and copolymers thereof. In one or more embodiments, one or more surfaces of the valve prosthesis and/or one or more of its components or portions may comprise, be covered with, be coated with, or be attached or coupled to one or more glues and/or adhesives, such as a bioglue or bioadhesive used to help anchor and/or seal the valve prosthesis to native tissue.

In one or more embodiments, one or more surfaces of the valve prosthesis and/or one or more of its components or portions may comprise, be covered with, be coated with, or be attached or coupled to one or more radioactive materials and/or biological agents, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and/or a dye (which acts as a biological ligand). Biological agents may be found in nature (naturally occurring) or may be chemically synthesized by a variety of methods well known in the art.

In one or more embodiments, valve prosthesis and/or one or more of its components or portions may comprise, be coated with, be covered with, or be attached or coupled to one or more biological cells or tissues, for example, tissue cells, cardiac cells, contractile cells, muscle cells, heart muscle cells, smooth muscle cells, skeletal muscle cells, autologous cells, allogenic cells, xenogenic cells, stem cells, genetically engineered cells, non-engineered cells, mixtures of cells, precursor cells, immunologically neutral cells, differentiated cells, undifferentiated cells, natural tissue, synthetic tissue, animal tissue, human tissue, porcine tissue, equine tissue, porcine tissue, bovine tissue, ovine tissue, autologous tissue, allogenic tissue, xenogenic tissue, autograft tissue, genetically engineered tissue, non-engineered tissue, mixtures of tissues, cardiac tissue, pericardial tissue, cardiac valve tissue, membranous tissue, and/or intestinal submucosa tissue. In one or more embodiments, valve prosthesis and/or one or more of its components or portions may comprise, be covered with, be coated with, or be attached or coupled to one or more materials that promote the growth of cells and/or tissue. In one or more embodiments, the cell and/or tissue promoting materials may comprise, possess or be configured to possess physical characteristics such as size, shape, porosity, matrix structure, fiber structure, and/or chemical characteristics such as growth factors, biological agents, that promote and/or aid, for example, in the adherence, proliferation and/or growth of desired cells and/or tissues in vivo following implantation or ex vivo prior to implantation. In one or more embodiments, the cell and/or tissue promoting materials may accelerate the healing response of the patient following the implantation of the valve prosthesis. In one or more embodiments, the cell and/or tissue promoting materials may comprise pockets, parachutes, voids, and/or openings, for example, that may trap cells and/or tissues and/or promote cells and/or tissues to proliferate, grow and/or heal.

In one or more embodiments, the valve prosthesis may comprise one or more active and/or passive fixation elements or members such as anchors, barbs, prongs, clips, grommets, sutures, and/or screws. In one or more embodiments, one or more active and/or passive fixation elements or members may be delivered separately from the valve prosthesis. In one or more embodiments, one or more active and/or passive fixation elements or members may be delivered during the valve prosthesis implant procedure. In one or more embodiments, one or more active and/or passive fixation elements or members may be delivered after the valve prosthesis implant procedure. In one or more embodiments, one or more active and/or passive fixation elements or members may be delivered using the valve prosthesis delivery system. In one or more embodiments, one or more active fixation elements or members may be activated by pushing, pulling, twisting, screwing and/or turning motion or movement. In one or more embodiments, one or more fixation elements or members may be released or engaged via an unsheathing, an unsleeving, a dissolving, and/or a degrading action. In one or more embodiments, one or more active and/or passive fixation elements or members may be delivered using a fixation element delivery system. In one or more embodiments, one or more active and/or passive fixation elements or members may be coupled, connected, and/or attached to the valve prosthesis stent or frame. In one or more embodiments, the valve prosthesis stent or frame may comprise a unitary structure that comprises one or more active and/or passive fixation elements. In one or more embodiments, one or more active and/or passive fixation elements may be coupled, connected, and/or attached to the valve prosthesis skirt and/or graft material. In one or more embodiments, one or more fixation elements or members may be designed to increasingly engage one or more heart tissues and/or structures via any movement of the valve prosthesis relative to heart tissue and/or structures during one or more cardiac cycles. For example, a barbed fixation element that further embeds itself into tissue via movement of the valve prosthesis relative to tissue in one direction and then resists movement of the valve prosthesis relative to tissue in the opposite direction.

In one or more embodiments, the valve prosthesis may comprise one or more posts or tabs 29 circumferentially spaced about a circumference defined by the stent frame. The posts or tabs can assume various forms, and in some embodiments are identical. One or more posts or tabs may comprise one or more slots or openings. The posts or tabs can be used to couple or retain the valve prosthesis to a valve deployment or delivery system.

In certain embodiments, the valve prosthesis is configured for repairing an aortic valve. Alternatively, other shapes are also envisioned to adapt to the specific anatomy of the valve to be repaired (e.g., stented prosthetic heart valves in accordance with the present disclosure can be shaped and/or sized for replacing a native aortic, mitral, pulmonic and/or tricuspid valve).

Valve prosthesis 20 described herein may be implanted into an annulus of a native cardiac valve via a suitable delivery route or procedure. For example, the valve prosthesis may be delivered through an artery or vein, a femoral artery, a femoral vein, a jugular vein, a subclavian artery, an axillary artery, an aorta, an atrium, and/or a ventricle. The valve prosthesis may be delivered via a transfemoral, transapical, transseptal, transatrial, transventrical, or transaortic procedure.

In some embodiments, an aortic valve prosthesis may be delivered transfemorally. In such a delivery, a delivery device and the valve prosthesis can be advanced in a retrograde manner through the femoral artery and into the patient's descending aorta. The delivery device and valve prosthesis can then be advanced under fluoroscopic guidance over the aortic arch, through the ascending aorta, and mid-way across the defective aortic valve. Once positioning of the catheter is confirmed, the delivery device can deploy the valve prosthesis within the defective valve in a stepped deployment procedure. The valve prosthesis can then expand against and align the prosthesis within the defective valve.

In some embodiments, a mitral valve prosthesis may be delivered transfemorally. In such a delivery, a delivery device and the valve prosthesis can be advanced in a retrograde manner through the femoral artery and into the patient's descending aorta. The delivery device and valve prosthesis can then be advanced under fluoroscopic guidance over the aortic arch, through the ascending aorta, into the left ventricle, and mid-way across the defective mitral valve. Once positioning of the catheter is confirmed, the delivery device can deploy the valve prosthesis within the defective valve in a stepped deployment procedure. The valve prosthesis can then expand against and align the prosthesis within the defective valve.

In some embodiments, a valve prosthesis can be delivered via a transapical procedure. In a transapical procedure, a delivery device and the valve prosthesis can be inserted into a patient's left ventricle through an incision created in the apex of the patient's heart. A dilator may be used to aid in the insertion of the delivery device and valve prosthesis. In this approach, the native valve (for example, a mitral valve or an aortic valve) may be approached from either a downstream direction relative to the blood flow for a mitral valve or an upstream direction relative to the blood flow for an aortic valve. The delivery device and valve prosthesis may be advanced mid-way across the defective valve. Once positioning of the catheter is confirmed, the delivery device can deploy the valve prosthesis within the defective valve in a stepped deployment procedure. The valve prosthesis can then expand against and align the prosthesis within the defective valve.

In some embodiments, a mitral valve prosthesis can be delivered via a transatrial procedure. In such a procedure, a delivery device and the valve prosthesis can be inserted through an incision made in the wall of the left atrium of the patient's heart. The delivery device and valve prosthesis may be advanced mid-way across the defective mitral valve. Once positioning of the catheter is confirmed, the delivery device can deploy the valve prosthesis within the defective valve in a stepped deployment procedure. The valve prosthesis can then expand against and align the prosthesis within the defective valve.

In some embodiments, an aortic valve prosthesis can be delivered via a transatrial procedure. In such a procedure, a delivery device and the valve prosthesis can be inserted through an incision made in the wall of the left atrium of the patient's heart. The delivery device and valve prosthesis may be advanced through the left atrium, through the mitral valve, into the left ventricle, and mid-way across the defective aortic valve. Once positioning of the catheter is confirmed, the delivery device can deploy the valve prosthesis within the defective valve in a stepped deployment procedure. The valve prosthesis can then expand against and align the prosthesis within the defective valve.

In one or more embodiments of the present invention, valve prosthesis and/or one or more of its components or portions may be delivered, for example, through a thoracotomy, a sternotomy, percutaneously, transvenously, arthroscopically, endoscopically, for example, through a percutaneous port, a stab wound or puncture, through a small incision, for example, in the chest, groin, abdomen, neck, leg, arm, or in combinations thereof. In one or more embodiments of the present invention, valve prosthesis and/or one or more of its components or portions may be delivered, for example, via a transvascular method, a transarterial method, a transvenous method, a transcardiac method, a transatrial method, a transventrical method, transapical method, a transseptal method, a transaortic method, a transcatheter method, a surgical method, a beating heart method, a stopped heart method, a pump-assisted method, and/or a cardiopulmonary bypass method.

In one or more embodiments of the present invention, valve prosthesis and/or one or more of its components or portions may be positioned in, positioned through, and/or positioned adjacent to, for example, a natural valve, a native valve, a synthetic valve, a replacement valve, a tissue valve, a mechanical valve, a mitral valve, an aortic valve, a pulmonary valve, a tricuspid valve, a valve component, a valve annulus, a valve leaflet, chordea, and/or a valve commissure.

In one or more embodiments, valve prosthesis 20 maybe delivered via a delivery system that comprises a catheter with a plurality of retractable sheaths or capsules that cover valve prosthesis 20 until it is to be deployed, at which point the sheaths may be retracted to allow the stent frame to self-expand. Further details of such embodiments are discussed below.

Figure 3A:
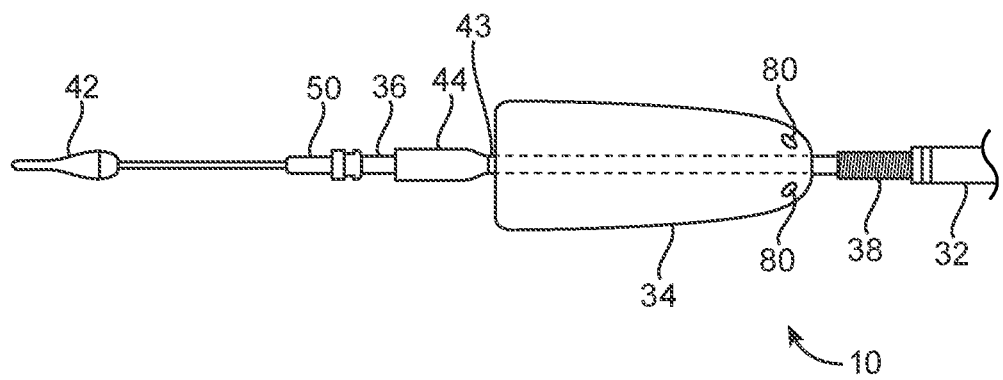
FIG. 3A is a side view of a prosthetic heart valve stepped deployment system in an initial configuration.
Figure 3B:
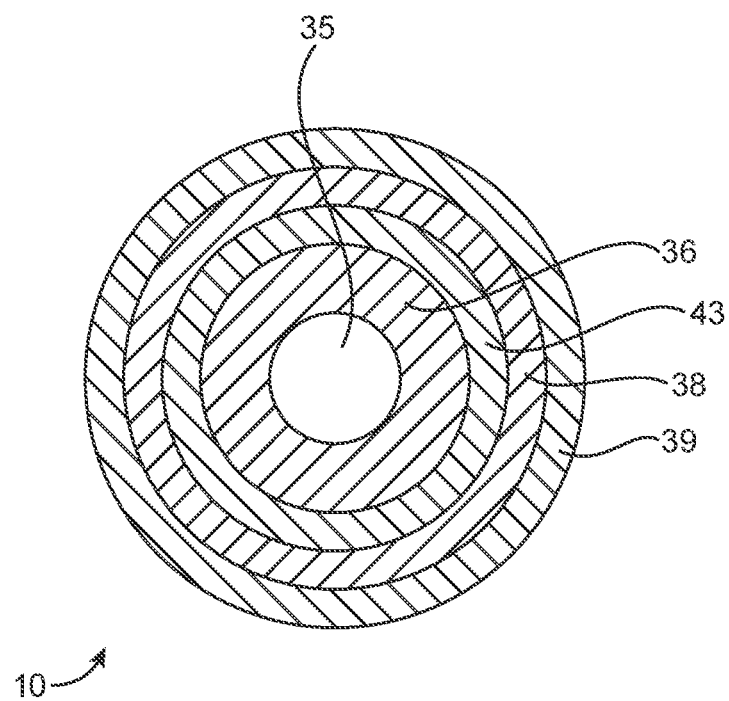
FIG. 3B is a cross-sectional view of a prosthetic heart valve stepped deployment system.

With the above understanding of the prosthetic heart valve 20 in mind, one embodiment of a prosthetic heart valve stepped deployment system 10 in accordance with the present disclosure is illustrated in FIGS. 3A and 3B. As a point of reference, although the prosthetic heart valve stepped deployment system 20 can be loaded with a stented prosthetic heart valve 20 for percutaneous delivery thereof, such a prosthesis is not shown in FIGS. 3A and 3B.

The prosthetic heart valve stepped deployment system 10 includes a primary capsule or sheath 32, a secondary capsule or sheath 34, an inner tube or shaft assembly 36 and a handle (not shown). Details on the various components are provided below.

Figure 7:
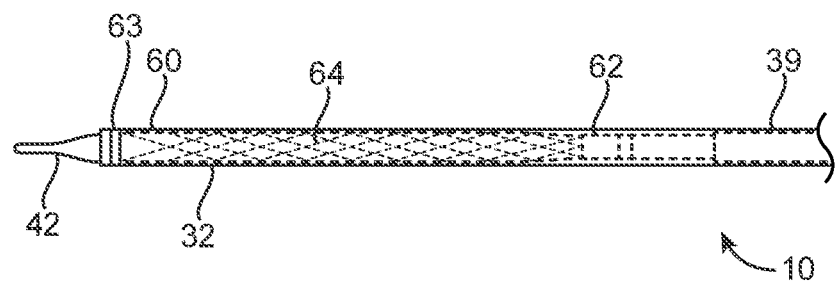
FIG. 7 is a side view of the prosthetic heart valve stepped deployment system of FIG. 1 after the compression sleeve has been removed therefrom, which is referred to as a loaded state.
Figure 9:
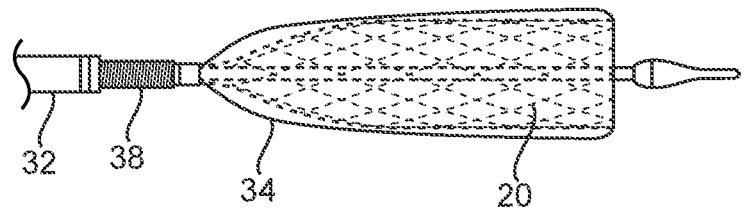
FIG. 9 is a side view of the prosthetic heart valve stepped deployment system of FIG. 1 in a partially deployed state after the primary capsule is moved to a retracted position.
Figure 13:
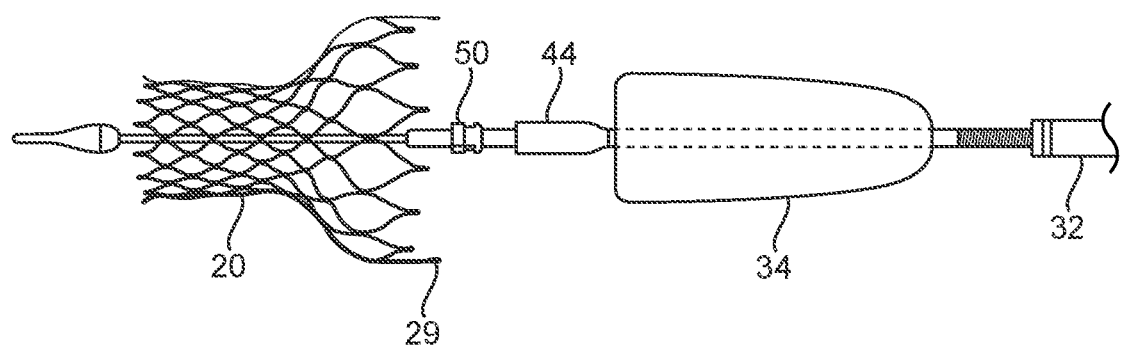
FIG. 13 is a side view of the prosthetic heart valve stepped deployment system of FIG. 1A separated from the prosthetic heart valve and where the prosthetic heart valve is in the expanded arrangement.

In some embodiments, the prosthetic heart valve stepped deployment system 10 is transitionable from a loaded state (as shown in FIG. 7) in which the stented prosthetic heart valve 20 is coupled to inner tube or shaft 36 while being contained within the primary capsule 32 and the secondary capsule 34, to a partially deployed state (as shown in FIG. 9) in which the primary capsule 32 is retracted from the prosthetic heart valve 20, thereby permitting the prosthetic heart valve 20 to partially self-expand (or alternatively be caused to partially expand by a separate mechanism such as a balloon) within the secondary capsule 34 thus allowing more accurate positioning of the prosthetic heart valve 20 within the native valve prior to full deployment of the prosthetic valve within the native valve. The secondary capsule 34 is then retracted and the prosthetic heart valve 20 is released from the prosthetic heart valve stepped deployment system 10 (as shown in FIG. 13). The prosthetic heart valve stepped deployment system 10 thereby provides a stepped deployment process that enhances the accuracy at which the prosthetic heart valve 20 is positioned.

The prosthetic heart valve stepped deployment system 10 can be used with a conventional introducer device (not shown). The prosthetic heart valve stepped deployment system 10 may utilize a variety of actuation mechanisms that control movement of the primary capsule 32 and secondary capsule 34 as well as release of the prosthetic heart valve 20. An example of one suitable actuation mechanism is disclosed in Tran et al., U.S. patent Publication No. 2011/0251680, the contents of which are incorporated herein by reference.

In certain embodiments, the actuation mechanism facilitates movement of the primary capsule 32 and the secondary capsule 34 and release of the prosthetic heart valve 20 from outside of the patient's body.

An inner tube or shaft assembly 36 can have various constructions appropriate for supporting a prosthetic heart valve 20 within primary and secondary capsules 32 and 34. The inner valve support tube or shaft assembly 36 may include one or more lumens 35 (as shown in FIG. 3B) extending from a distal end to a proximal end thereof. In one embodiment, the inner valve support tube assembly 36 may comprise a lumen 35 for passing a guidewire therethrough. The inner tube assembly 36 extends distally from a stepped deployment system handle. One or more portions of the inner tube assembly 36 may be formed as a braided tube. For example, one or more portions of the inner tube assembly 36 may be a thermoplastic elastomer, such as Pebax®, with an embedded braided metal layer constructed from stainless steel wire. Other configurations are also acceptable, with the inner tube assembly 36 serving to couple valve prosthesis 20 to the deployment valve prosthesis delivery system 10.

In some embodiments, the distal end portion of inner valve support tube assembly 36 comprises a hub or spindle member 50 configured to comprise one or more tabs or slots for assisting in retaining the valve prosthesis until full deployment. Hub member 50 comprises one or more features, e.g., tabs or slots, for engaging one or more prosthetic heart valve 20 features, e.g., posts or tabs 29. Depending upon the configuration and arrangement, as well as semantics, the tabs may be described as projecting ears, buttons, or hooks.

In some embodiments, the distal end portion of inner tube assembly 36 comprises a tapered nose piece, cone or tip 42 mounted at the distal end, which allows the delivery or deployment system to easily pass through the native vascular system and to easily cross the native valve atraumatically. In certain embodiments, tip 42 may comprise a lumen, e.g., for passing a guidewire therethrough.

In some embodiments, the inner tube assembly 36 is constructed to be sufficiently flexible for passage through a patient's vasculature yet exhibits sufficient longitudinal rigidity to effectuate desired axial movement of the inner tube assembly 36.

In some embodiments, delivery system 10 comprises a valve retainer tube or sheath assembly 43 slidably disposed over inner tube assembly 36 wherein the inner tube assembly 36 resides within a lumen of valve retainer tube assembly 43. Valve retainer tube assembly 43 can move relative to inner tube assembly 36. The distal end portion of valve retainer tube assembly 43 comprises a valve retainer sleeve member 44. Valve retainer sleeve 44 is advanced over hub or spindle member 50 and one or more portions of valve prosthesis 20, e.g., valve prosthesis posts or tabs 29, which are coupled to or retained by hub or spindle member 50. Valve retainer member 44 helps to secure or retain the valve prosthesis to the delivery system until full deployment of the valve prosthesis, which occurs when valve retainer sleeve 44 is retracted from covering the hub or spindle member 50 and valve prosthesis 20, thereby allowing valve prosthesis 20 to be released from delivery system 10. The valve retainer tube assembly 43 extends distally from a stepped deployment system handle. One or more portions of the valve retainer tube assembly 43 may be formed as a braided tube. For example, one or more portions of the valve retainer tube assembly 43 may be a thermoplastic elastomer, such as Pebax®, with an embedded braided metal layer constructed from stainless steel wire. Other configurations are also acceptable, with the valve retainer tube assembly 43 serving to help retain valve prosthesis 20 to the deployment valve prosthesis delivery system 10.

In some embodiments, the valve retainer tube assembly 43 is constructed to be sufficiently flexible for passage through a patient's vasculature yet exhibits sufficient longitudinal rigidity to effectuate desired axial movement of the valve retainer member 44. In certain embodiments, movement of the proximal end of the valve retainer tube assembly 43 is directly transferred to the valve retainer member 44 and causes a corresponding movement of the valve retainer member 44. For example, proximal movement of the proximal end of the valve retainer tube assembly 43 may be directly transferred to the valve retainer member 44 and causes a corresponding proximal movement of the valve retainer member 44. Likewise, distal movement of the proximal end of the valve retainer tube assembly 43 may be directly transferred to the valve retainer member 44 and causes a corresponding distal movement of the valve retainer member 44. In some embodiments, the valve retainer tube assembly 43 is further configured to transmit a rotational force or movement onto the valve retainer member 44.

In certain embodiments, delivery system 10 comprises a central tube or sheath assembly 38 comprising a secondary capsule 34 at its distal end. In certain embodiments, the secondary capsule 34 is defined as a continuation of central tube assembly 38, with the central tube assembly 38 being coupled to one end of the secondary capsule 34 at a connection point. The secondary capsule 34 may be coupled to central tube 38 via heat and/or adhesive bonding, for example.

In some embodiments, central tube or sheath assembly 38 is slidably disposed over valve retainer tube assembly 43 wherein the valve retainer tube assembly 43 resides within a lumen of central tube assembly 38. Central tube assembly 38 can move relative to valve retainer tube assembly 43. The distal end portion of central tube assembly 38 comprises secondary capsule 34. The central tube assembly 38 extends distally from a stepped deployment system handle. One or more portions of the central tube assembly 38 may be formed as a braided tube. For example, one or more portions of the central tube assembly 38 may be a thermoplastic elastomer, such as Pebax®, with an embedded braided metal layer constructed from stainless steel wire. Other configurations are also acceptable, with the central tube assembly 38 serving to help deploy valve prosthesis 20 in a stepwise deployment procedure.

In some embodiments, the central tube assembly 38 is constructed to be sufficiently flexible for passage through a patient's vasculature yet exhibits sufficient longitudinal rigidity to effectuate desired axial movement of the secondary capsule 34.

In some embodiments, movement of the proximal end of the central tube assembly 38 may be directly transferred to the secondary capsule 34 and causes a corresponding movement of the secondary capsule 34. For example, proximal movement of the proximal end of the central tube assembly 38 is directly transferred to the secondary capsule 34 and causes a corresponding proximal of the secondary capsule 34. Likewise, distal movement of the proximal end of the central tube assembly 38 is directly transferred to the secondary capsule 34 and causes a corresponding distal movement of the secondary capsule 34. In some embodiments, the central tube assembly 38 is further configured to transmit a rotational force or movement onto the secondary capsule 34.

The inner tube assembly 36 can assume a variety of forms appropriate for supporting a stented prosthetic heart valve within the primary and secondary capsules 32 and 34. For example, the inner tube assembly 36 can include a valve tab retainer hub 50. In general terms, the valve tab retainer hub 50 incorporates features for retaining the stented prosthetic heart valve 20 within the primary and secondary capsules 32 and 34 as described below.

In some embodiments, delivery system 10 comprises an outer tube or sheath assembly 39 comprising a primary capsule 32 at its distal end. In certain embodiments, the primary capsule 32 is defined as a continuation of outer tube assembly 39, with the outer tube assembly 39 being coupled to one end of the primary capsule 32 at a connection point. The primary capsule 32 may be coupled to outer tube assembly 39 via heat and/or adhesive bonding, for example.

In some embodiments, outer tube assembly 39 is slidably disposed over central tube assembly 38 wherein the central tube assembly 38 resides within a lumen of outer tube assembly 39. Outer tube assembly 39 can move relative to central tube assembly 38. The distal end portion of outer tube assembly 39 comprises primary capsule 32. The outer tube assembly 39 extends distally from a stepped deployment system handle. One or more portions of the outer tube assembly 39 may be formed as a braided tube. For example, one or more portions of the outer tube assembly 39 may be a thermoplastic elastomer, such as Pebax®, with an embedded braided metal layer constructed from stainless steel wire. Other configurations are also acceptable, with the outer tube assembly 39 serving to help deploy valve prosthesis 20 in a stepwise deployment procedure.

In some embodiments, the outer tube assembly 39 is constructed to be sufficiently flexible for passage through a patient's vasculature yet exhibits sufficient longitudinal rigidity to effectuate desired axial movement of the primary capsule 32.

In some embodiments, movement of the proximal end of the outer tube assembly 39 may be directly transferred to the primary capsule 32 and causes a corresponding movement of the primary capsule 32. For example, proximal movement of the proximal end of the outer tube assembly 39 may be directly transferred to the primary capsule 32 and causes a corresponding proximal movement of the primary capsule 32. Likewise, distal movement of the proximal end of the outer tube assembly 39 may be directly transferred to the primary capsule 32 and causes a corresponding distal movement of the primary capsule 32. In some embodiments, the outer tube assembly 39 is further configured to transmit a rotational force or movement onto the primary capsule 32.

In some embodiments, the primary capsule 32 is constructed to compressively retain the self-expanding, prosthetic heart valve 20 in a collapsed arrangement. In certain embodiments, the primary capsule 32 includes or defines a distal segment or portion 60 and a proximal segment or portion 62 (as shown in FIG. 7).

The distal segment 60 can terminate at the distal end 42 of the inner tube assembly 36. In certain embodiments, the distal segment 60 may comprise a radiopaque marker 63. In other embodiments, an additional tubular structure is provided distal the distal segment 60 (e.g., polymer tubing carrying a radiopaque marker) that is not intended or constructed to compressively retain the prosthetic heart valve 20 in the loaded state, and thus is not part of the primary capsule 32.

The primary capsule 32 can be formed as a continuation of the outer tube assembly 39. Alternatively, the primary capsule 32 and the outer tube assembly 39 can have differing constructions. In certain embodiments, construction of the distal segment 60 differs from that of the proximal segment 62 so as to generate a connection point or intermediate zone or segment 64 between the segments 60, 62.

In some embodiments, the axial length of the primary capsule 32 is selected in accordance with the axial length of the prosthetic heart valve 20 to be loaded within the prosthetic heart valve stepped deployment system 10 as described below. In certain embodiments, the axial length of the primary capsule 32 is equal to, less than, or greater than the axial length of the prosthetic heart valve 20.

In some embodiments, the differing constructions of the distal, proximal, and intermediate segments 60, 62, 64 can assume various forms. For example, in some constructions, an outer diameter of the distal segment 60 is greater than an outer diameter of the proximal segment 62 or an outer diameter of the proximal segment 62 is greater than an outer diameter of the distal segment 60. Further, an inner diameter of the distal segment 60 can be greater than an inner diameter of the proximal segment 62 or an inner diameter of the proximal segment 62 can be greater than an inner diameter of the distal segment 60. In some constructions, the intermediate segment 64 may have an outer diameter greater than an outer diameter of the distal segment 60 and/or the proximal segment 62.

In some embodiments, the distal segment 60 may comprise a cut metal tube (e.g., a laser-cut hypotube) embedded or encapsulated within a polymer (e.g., Pebax®), whereas the proximal segment 62 may comprise a braided polymer tube. In some embodiments, the distal, intermediate, and proximal segments 60, 62, 64 may be formed of a similar material (e.g., a polymer tube, braided tube, etc.). Other acceptable constructions of one or more portions of the primary capsule 32 include high strength polymeric materials (e.g., polyamide, PEEK, etc.).

In embodiments where the proximal segment 62 is formed or defined as a homogenous continuation of the outer tube assembly 39, a perceptible demarcation between the proximal segment 62 and the outer tube assembly 39 may not exist. When loaded with the prosthetic heart valve 20, however, a portion of the outer tube assembly 39 may extend over a region of the prosthetic heart valve 20 and can be viewed as defining the proximal segment 62 of the primary capsule 32.

In contrast to the primary capsule 32, which has to be relatively strong to retain the prosthetic heart valve 20 in a compressed arrangement, the secondary capsule 34 needs only to be strong enough to retain the prosthetic valve 20 in a semi-compressed arrangement and needs only to be strong enough to prevent the prosthetic heart valve 20 from fixedly engaging the native valve tissue while the valve is being deployed. As such, the secondary capsule 34 may be fabricated from a flexible and relatively thin material such as a polymer or plastic. The flexible and relatively thin nature of the secondary capsule 34 enhances the ability of the secondary capsule 34 to be positioned in the primary capsule 32 while minimizing the additional space in the primary capsule 32 that is occupied by the secondary capsule 34.

While it is illustrated in the drawings that the secondary capsule 34 is transparent, it is possible for the secondary capsule 34 to be fabricated from a non-transparent material.

Additionally, while it is illustrated that the secondary capsule 34 is fabricated from a non-woven sheet of material, it is also possible to fabricate the secondary capsule 34 from a woven material.

The secondary capsule 34 should be sufficiently strong to resist tearing or other damage while the primary capsule 32 is moved onto and off of the secondary capsule 34 as well as when the secondary capsule 34 is moved onto and off of the prosthetic heart valve 20 as well as when the secondary capsule 34 is withdrawn from between the expanded prosthetic heart valve 20 and native valve tissue. However, as noted above, the secondary capsule 34 does not need to be sufficiently strong to retain the prosthetic heart valve 20 in the loaded compressed arrangement.

In certain embodiments, the secondary capsule 34 has a diameter that is less than the diameter of the region where the prosthetic heart valve 20 is being implanted so that the secondary capsule 34 becomes taut when the prosthetic heart valve 20 is in a partially deployed arrangement. In certain embodiments, the secondary capsule 34 has a diameter that is greater than the diameter of the region where the prosthetic heart valve 20 is being implanted so that the secondary capsule 34 does not become taut when the prosthetic heart valve 20 is in a partially deployed arrangement.

In certain embodiments, the partially deployed arrangement is expanded to at least about 70% of the expanded deployed arrangement. In other embodiments, the partially deployed arrangement is expanded to at least about 90% of the expanded deployed arrangement.

The secondary capsule 34 allows the prosthetic heart valve 20 to move or expand to the partially deployed arrangement. When the prosthetic heart valve 20 is in the partially deployed arrangement, the prosthetic heart valve 20 is less compressed than the compressed arrangement but more compressed than the deployed arrangement.

When the prosthetic heart valve 20 is in the partially deployed arrangement, it is possible to evaluate the position of the prosthetic heart valve 20 because the secondary capsule 34 enables the prosthetic heart valve 20 to be moved with respect to native valve tissue, e.g., the native valve annulus.

In certain embodiments, the valve and secondary capsule are designed such that the valve is in a functioning state (i.e. it opens and closes in concert with the heartbeat in a manner similar to its performance during full deployment) while the valve is retained by the secondary capsule. The secondary capsule 34 includes at least one aperture 80 formed therein. In certain embodiments, there are a plurality of apertures 80 formed in the secondary capsule 34. The apertures 80 allow blood to flow through the secondary capsule 34 but should not impact the structural integrity of the secondary capsule 34.

In certain embodiments, the apertures 80 are positioned proximate a proximal end of the secondary capsule 34. The apertures 80 may be arranged in a spaced-apart configuration around the secondary capsule 34.

When the prosthetic heart valve 20 is in the partially deployed arrangement, the apertures 80 in the secondary capsule 34 allow blood to flow through the prosthetic heart valve 20 similar to the flow of blood through the prosthetic heart valve 20 in the deployed arrangement prior to the prosthetic heart valve 20 engaging native valve tissue, e.g., the native valve annulus, when in the deployed arrangement.

Figure 4:
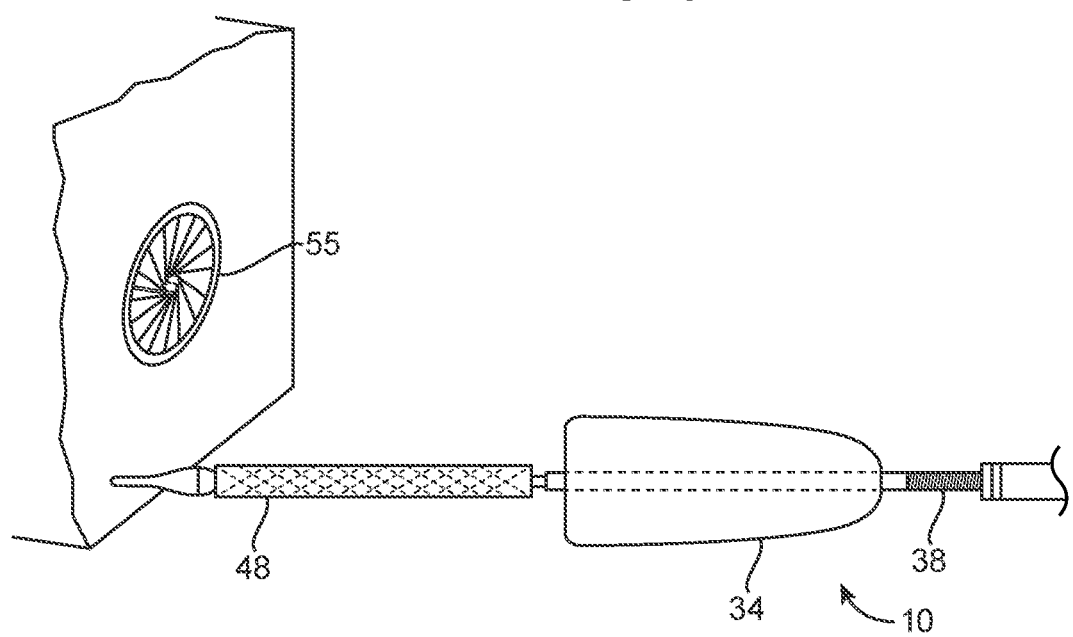
FIG. 4 is a side view of the prosthetic heart valve stepped deployment system of FIG. 1 with a compression sleeve placed thereon.

In operation, in one embodiment of utilizing the prosthetic heart valve deployment system 10, the components are loaded into a compressed arrangement. One suitable device for compressing the prosthetic heart valve is an iris crimper 55, as shown in FIG. 4.

Figure 5:
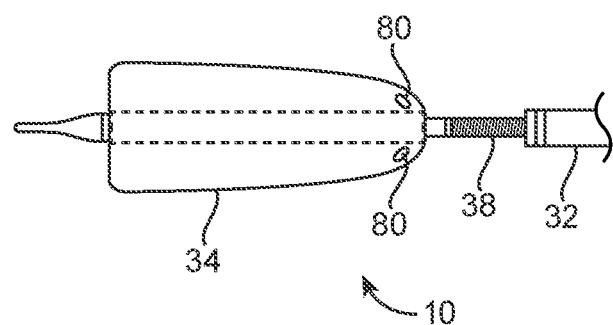
FIG. 5 is a side view of the prosthetic heart valve stepped deployment system of FIG. 1 with a secondary capsule positioned over the compression sleeve.
Figure 6:
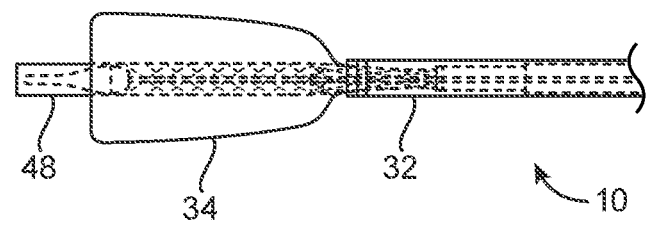
FIG. 6 is a side view of the prosthetic heart valve stepped deployment system of FIG. 1 with a primary capsule partially positioned over the secondary capsule.

In certain embodiments, upon crimping or compressing of the valve prosthesis, e.g., with an iris crimper, tabs 29 of the valve prosthesis stent frame 22 are engaged with retainer hub 50 of inner tube 36. Valve retainer tube assembly 43 is then advanced distally so that valve retainer sleeve 44 covers valve tabs 29 and retainer hub 50, thereby securing valve prosthesis 20 to valve deployment system 10. A compression sleeve 48 is then moved into position substantially covering the prosthetic heart valve 20, as illustrated in FIG. 4. In certain embodiments, the compression sleeve 48 is a Teflon tube. The secondary capsule 34 is then moved towards the distal end of the prosthetic heart valve deployment system 10 until the secondary capsule 34 covers compression sleeve 48, as illustrated in FIG. 5. Next, the primary capsule 32 is slowly moved or advanced distally over the secondary capsule 34 while the compression sleeve 48 is slowly moved or advanced distally off of valve prosthesis 20, as illustrated in FIG. 6.

Figure 8:
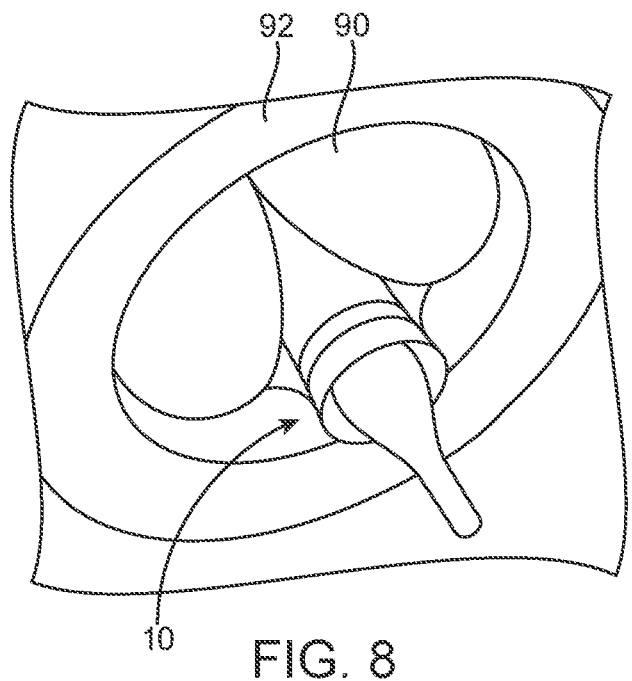
FIG. 8 is a perspective view of a distal end of prosthetic heart valve stepped deployment system of FIG. 1A advanced across a heart valve.

Once the primary capsule 32 is positioned over the secondary capsule 34 and the compression sleeve 48 has been removed, the prosthetic heart valve deployment system 10 is loaded, as illustrated in FIG. 7. In one embodiment, after appropriate preparation of the patient, the distal end of the prosthetic heart valve deployment system 10 is advanced through the patient's vascular system and advanced across the native aortic valve. FIG. 8 illustrates the distal end of the prosthetic heart valve deployment system 10 just beyond the leaflets 90 of the native aortic valve 92.

In one embodiment, both capsules 32, 34 and the prosthetic heart valve 20 are advanced (or partially advanced) into the left ventricle. The secondary capsule 34 and the prosthetic heart valve 20 are maintained in a substantially stationary position as the primary capsule 32 is retracted proximally.

In another embodiment, the primary capsule 32 is maintained in a substantially stationary position as the secondary capsule 34 and the prosthetic heart valve 20 are advanced distally into the left ventricle.

In both of the preceding configurations, the prosthetic heart valve 20 expands within the secondary capsule 34 from the compressed arrangement as the primary capsule 32 moves off the prosthetic heart valve 20. The prosthetic heart valve 20 in the partially expanded arrangement with the secondary capsule 34 positioned thereover is illustrated in FIG. 9.

The apertures 80 in the secondary capsule 34 permit blood to flow through the prosthetic heart valve 20. As such, once prosthetic heart valve 20 is in the partially expanded arrangement, the operation and location of the prosthetic heart valve 20 can be evaluated prior to the prosthetic heart valve 20 moving into the deployed arrangement.

Figure 10:
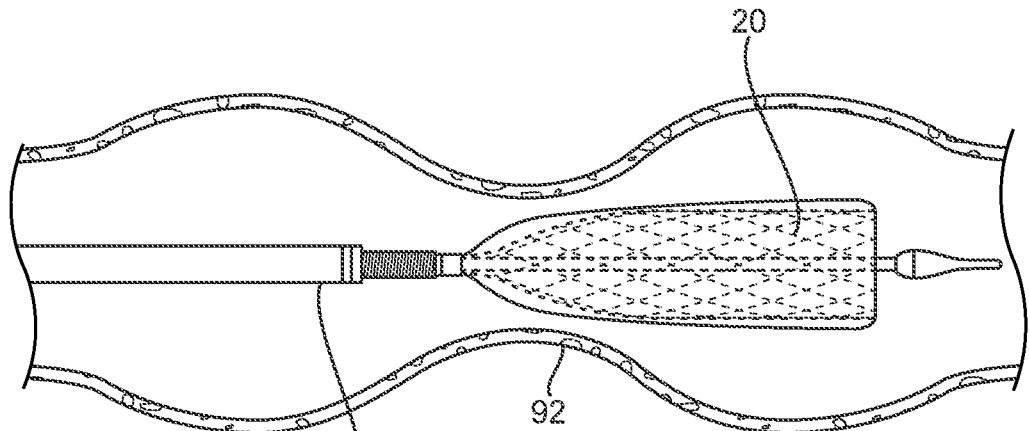
FIG. 10 is a side view of the prosthetic heart valve stepped deployment system of FIG. 1A in the partially deployed state and where the prosthetic heart valve is in an initial position with respect to a native annulus.
Figure 11:
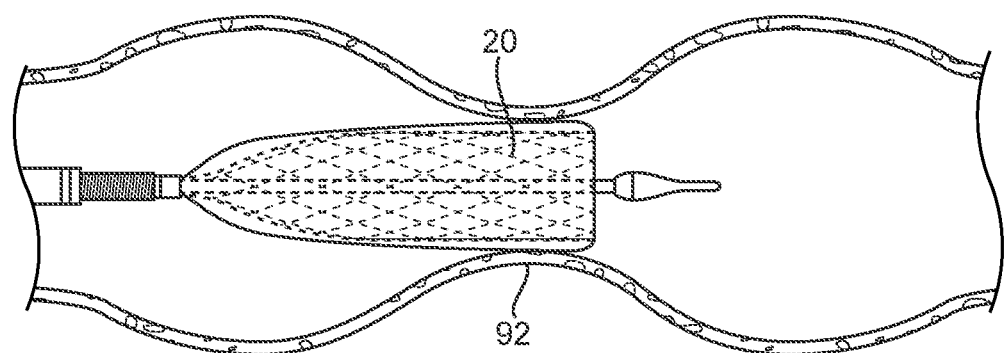
FIG. 11 is a side view of the prosthetic heart valve stepped deployment system of FIG. 1A in the partially deployed state and where the prosthetic heart valve is in a final position with respect to the native annulus.

In certain embodiments, the prosthetic heart valve 20 is first inserted into the left ventricle past the aortic annulus 92 to facilitate positioning of the prosthetic heart valve 20 in a desired position with respect to the native aortic valve 90 as illustrated in FIG. 10. The prosthetic heart valve 20 may then be moved in a proximal direction until the prosthetic heart valve 20 is in a desired position within the native aortic valve 90, as illustrated in FIG. 11. A person of skill in the art will appreciate that a variety of techniques may be used to evaluate the positioning of the prosthetic heart valve 20 relative to the native aortic valve 90.

Figure 12:
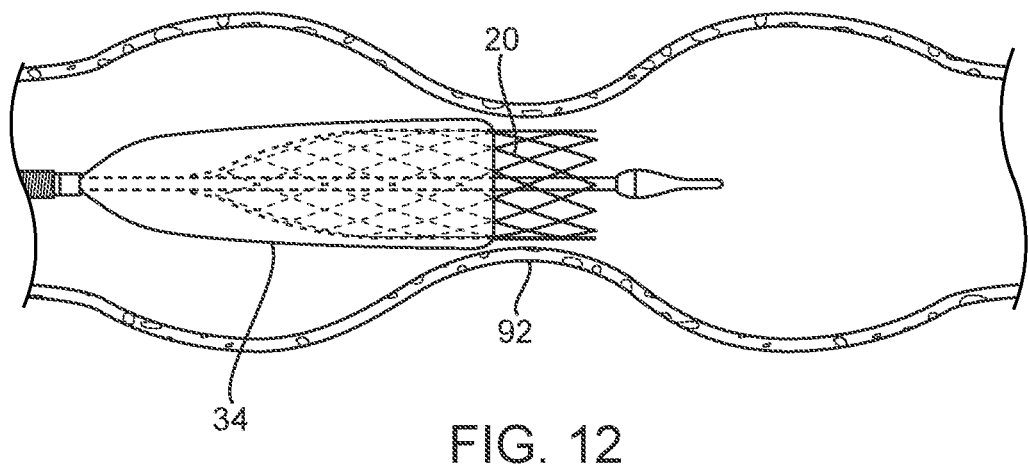
FIG. 12 is a side view of the prosthetic heart valve stepped deployment system of FIG. 1 where the secondary capsule is in a partially retracted position.

Next, the secondary capsule 34 is retracted in a proximal direction as illustrated in FIG. 12. The inner shaft assembly 36, which is attached to the outflow end of the prosthetic heart valve 20, is held in a substantially stationary position during the process of retracting the secondary capsule 34 so that the associated prosthetic heart 20 remains in the desired position with respect to the native heart valve.

To release the prosthetic heart valve 20, the valve retainer sleeve 44 is retracted proximally uncovering retainer hub 50 and valve tabs 29, which causes the prosthetic heart valve 20 to be released from the prosthetic heart valve deployment system 10, as illustrated in FIG. 13. The prosthetic heart valve deployment system 10 is then removed from the patient to complete the procedure.

Figure 14:
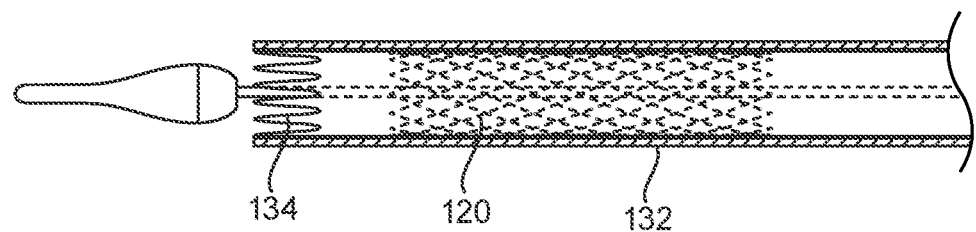
FIG. 14 is a side view of an alternative embodiment of the prosthetic heart valve stepped deployment system in a loaded state.
Figure 15:
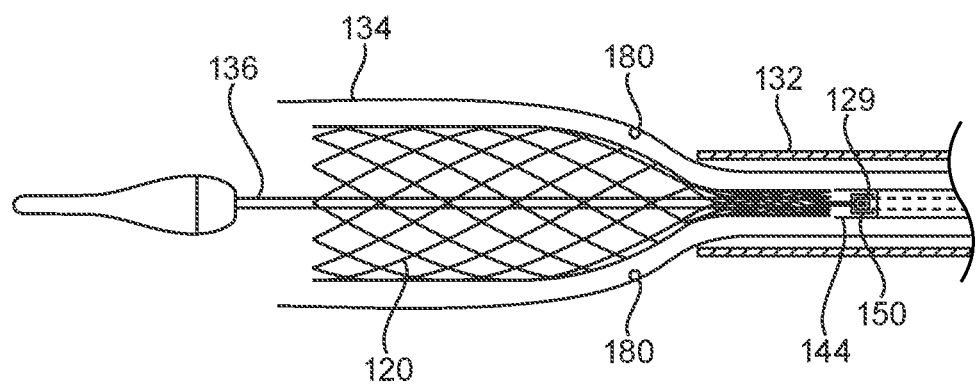
FIG. 15 is a side view of the prosthetic heart valve stepped deployment system of FIG. 14 in a partially deployed state.

Another embodiment of the prosthetic heart valve deployment system 110 is illustrated in FIGS. 14 and 15. The secondary capsule 134 is attached to the primary capsule 132 proximate a distal end thereof. In certain embodiments, the secondary capsule 134 is attached to the distal end of the primary capsule 132.

When the primary capsule 132 is in the extended position covering prosthetic heart valve 20 (illustrated in FIG. 14), the secondary capsule 134 is packed within the primary capsule 132 proximate the distal end thereof. In certain embodiments, the secondary capsule 134 is packed within the primary capsule 132 adjacent a distal end of the compressed prosthetic heart valve 120.

In this configuration, the primary capsule 132 is formed with a greater length than is needed to cover the prosthetic heart valve 120 so that the primary capsule 132 substantially covers the secondary capsule 134 when in the extended position.

As the prosthetic heart valve 120 is advanced from the end of the primary capsule 132 or as the primary capsule 132 is retracted from the extended position, the secondary capsule 134 is unpacked as illustrated in FIG. 15.

The secondary capsule 134 permits the prosthetic heart valve 120 to expand from the compressed arrangement to a partially expanded arrangement. However, the secondary capsule 134 prevents the prosthetic heart valve 120 from engaging the native tissue.

The secondary capsule 134 thereby permits the location of the prosthetic heart valve 120 to be evaluated and adjusted if needed. The apertures 180 in the secondary capsule 134 permit blood to flow through the prosthetic heart valve 120 when the prosthetic heart valve 120 is in the partially deployed arrangement to thereby further evaluate the performance and positioning of the prosthetic heart valve 120.

Once it is determined that the prosthetic heart valve 120 has been accurately positioned and is operating correctly, the primary capsule 132 is further retracted until the secondary capsule 134 is withdrawn from over the prosthetic heart valve 120. The inner shaft assembly 136, which is attached to the outflow end of the prosthetic heart valve 120, is held in a substantially stationary position during the process of retracting the secondary capsule 134 so that the associated prosthetic heart 120 remains in the desired position with respect to the native heart valve.

To release the prosthetic heart valve 120 the valve retainer sleeve 144 is retracted proximally uncovering retainer hub 150 and valve tabs 129, which causes the prosthetic heart valve 120 to be released from the prosthetic heart valve deployment system.

Figure 16:
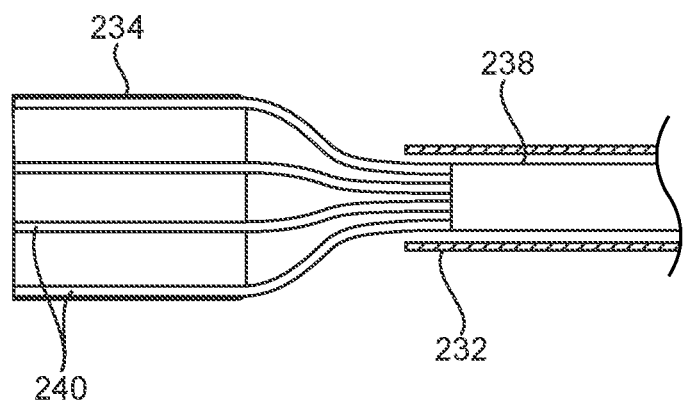
FIG. 16 is a side view of another alternative embodiment of the prosthetic heart valve stepped deployment system in a partially deployed state.

Another embodiment of the prosthetic heart valve deployment system 210 is illustrated in FIG. 16, which shows the primary capsule 232 in a retracted position and the secondary capsule 234 in an expanded configuration. In this embodiment, central tube assembly 238 may comprise a plurality of support spines 240 at its distal end to enhance the ability of the secondary capsule 234 to maintain its axial profile. In addition, as illustrated in FIG. 16, secondary capsule 234 may comprise a thin-walled band of material, e.g., attached to the inner surfaces of the distal end portion of support spines 240, such that in an expanded configuration blood can flow through the secondary capsule and in between the support spines 240 at a location proximal to the secondary capsule.

Figure 17:
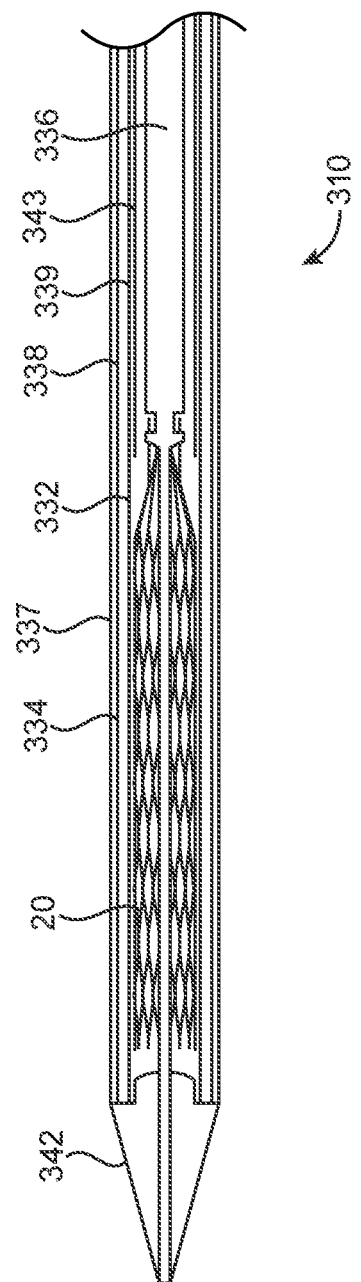
FIG. 17 is a side view of an alternative embodiment of the prosthetic heart valve stepped deployment system in a loaded state.
Figure 18:
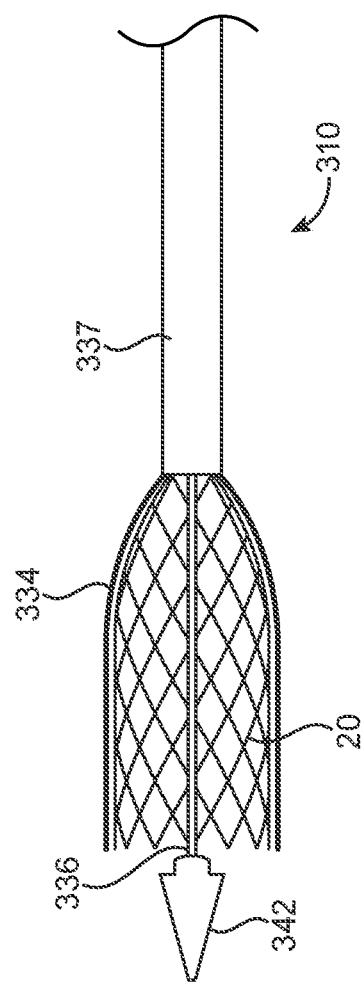
FIG. 18 is a side view of the prosthetic heart valve stepped deployment system of FIG. 17 in a partially deployed state.
Figure 19:
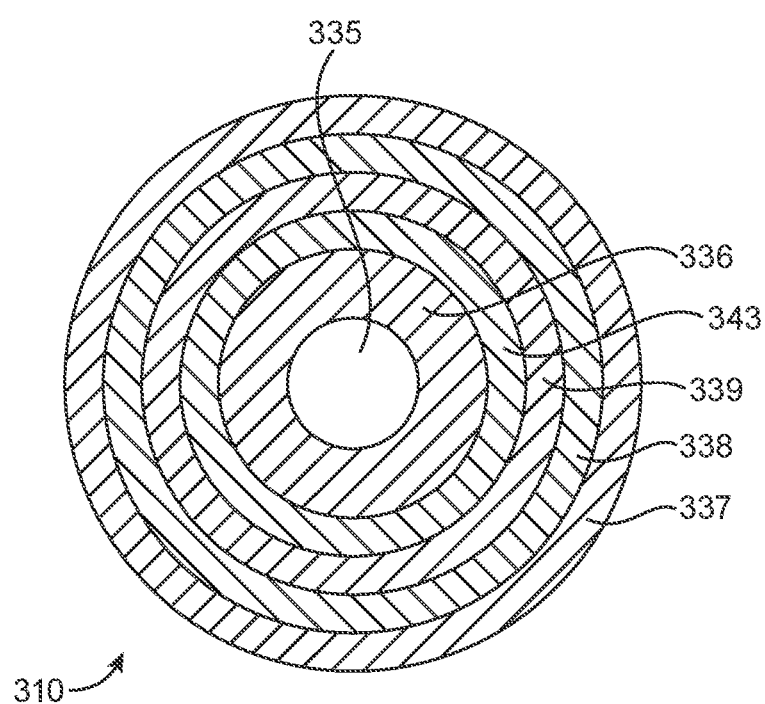
FIG. 19 is a cross-sectional view of the prosthetic heart valve stepped deployment system of FIG. 17.

Another embodiment of the prosthetic heart valve deployment system 310 is illustrated in FIGS. 17-19. FIG. 17 illustrates heart valve deployment system 310 in a loaded state or configuration. FIG. 18 illustrates heart valve deployment system 310 in a partially deployed state or configuration. FIG. 19 is a cross sectional view of the heart valve deployment system 310. Tube assembly 338 is slidably disposed over tube assembly 339 wherein tube assembly 339 resides within a lumen of tube assembly 338. Tube assembly 338 can move relative to tube assembly 339. Tube assembly 338 comprises a secondary capsule 334 at its distal end and tube assembly 339 comprises a primary capsule 332 at its distal end. The tube assemblies 338 and 339 extend distally from a stepped deployment system handle. One or more portions of the tube assemblies 338 and 339 may be formed as a braided tube. For example, one or more portions of the tube assemblies 338 and 339 may be a thermoplastic elastomer, such as Pebax®, with an embedded braided metal layer constructed from stainless steel wire. Other configurations are also acceptable, with the tube assemblies 338 and 339 serving to help deploy valve prosthesis 320 in a stepwise deployment procedure. Tube assembly 339 is slidably disposed over valve retainer tube assembly 343 wherein tube assembly 343 resides within a lumen of tube assembly 339. Tube assembly 339 can move relative to retainer tube assembly 343. Valve retainer tube assembly 343 is slidably disposed over inner tube assembly 336 wherein tube assembly 336 resides within a lumen of tube assembly 343. Valve retainer tube assembly 343 can move relative to inner tube assembly 336. Inner tube assembly 336 may comprise a guidewire lumen 335. Heart valve deployment system 310 comprises an outer tube or sheath assembly 337 slidably disposed over tube assembly 338 including the secondary capsule 334 wherein tube assembly 338 resides within a lumen of tube assembly 337. Tube assembly 337 can move relative to tube assembly 338. In some embodiments, the secondary capsule 334 may be placed in a lower profile behind the primary capsule 332. The secondary capsule 334 may be advanced over the primary capsule 332. In certain embodiments, the secondary capsule 334 is retained in an expandable sheath or tube assembly 337 to facilitate advancing the secondary capsule 334 across the native valve.

Figure 20:
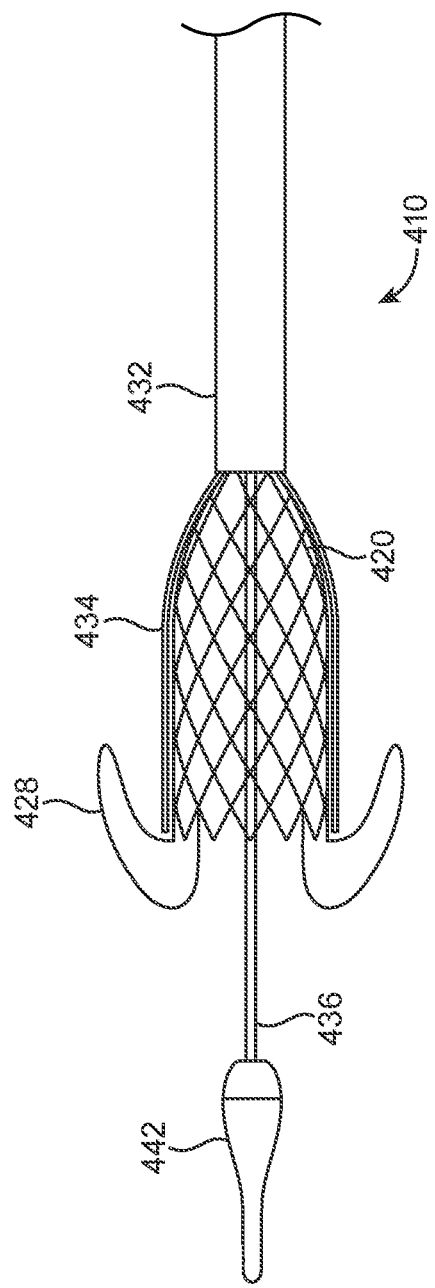
FIG. 20 is a side view of another alternative embodiment of the prosthetic heart valve stepped deployment system in a partially deployed state.

Another embodiment of the prosthetic heart valve deployment system 410 is illustrated in FIG. 20 wherein prosthetic heart valve deployment system 410 is shown in a partially deployed state. A prosthetic valve 420 comprising support arms 428 is shown partially expanded within secondary capsule 434. Primary capsule 432 is shown in a retracted state in that the primary capsule 432 has been moved proximally to uncover secondary capsule 434 and thereby allow prosthetic heart valve 420 to partially expand within secondary capsule 434. In some embodiments, the axial length of the secondary capsule 434 is selected in accordance with the axial length of the prosthetic heart valve 420 to be loaded within the prosthetic heart valve stepped deployment system 410. In certain embodiments, the axial length of the secondary capsule 434 is equal to, less than, or greater than the axial length of the prosthetic heart valve 420. For example, FIG. 20 shows the secondary capsule 434 partially covering or retaining prosthetic heart valve 420 in a partially deployed state in that a portion of valve 420 has fully expanded and a portion of valve 420 has only partially expanded within the secondary capsule 434. Support arms 428 of prosthetic heart valve 420 have fully expand upon the proximal retraction of the primary capsule 432. In one embodiment, the axial length of the secondary capsule is less than prosthetic heart valve 420 loaded within the valve delivery system 410. For example, the secondary capsule 434 may not cover the support arms 428 of valve 420 in both the loaded state and the partially deployed state. In one embodiment, the axial length of the secondary capsule is equal to or greater than prosthetic heart valve 420 loaded within the valve delivery system 410. The secondary capsule 434 may be retracted proximally to uncover in a gradual manner the partially expanded or deployed valve 420. The ability to partially expand one or more portions of a prosthetic valve while allowing one or more portions of the valve to fully expand during delivery of the valve can be beneficial in the positioning and/or placement of the valve within the patient.

Figure 21:
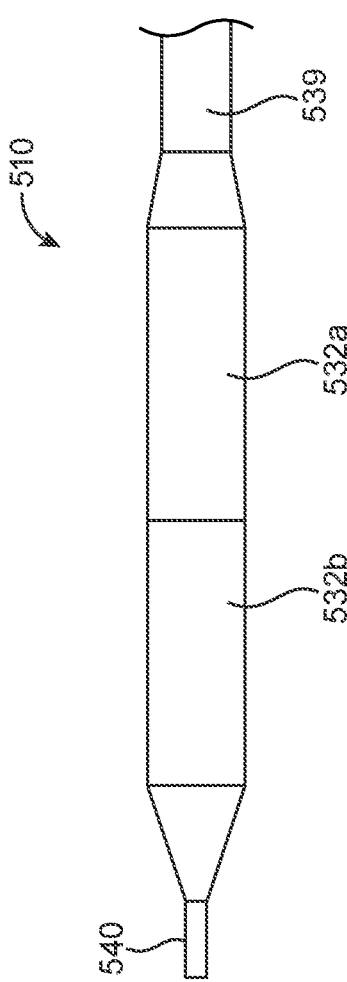
FIG. 21 is a side view of another alternative embodiment of the prosthetic heart valve stepped deployment system in a loaded state.
Figure 22:
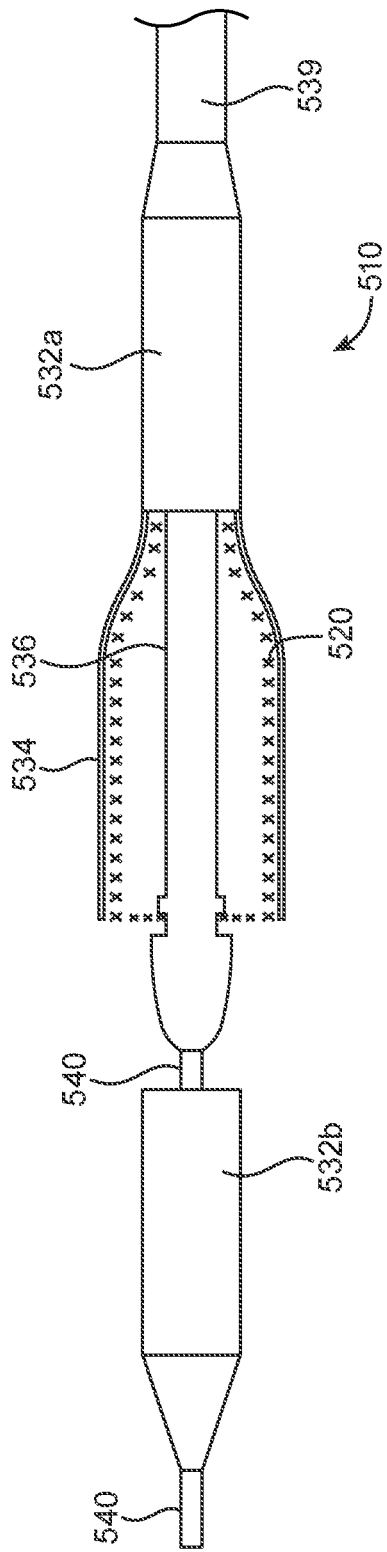
FIG. 22 is a side view of the prosthetic heart valve stepped deployment system of FIG. 21 in a partially deployed state.

Another embodiment of the prosthetic heart valve deployment system 510 is illustrated in FIGS. 21 and 22. FIG. 21 illustrates heart valve deployment system 510 in a loaded state or configuration. In some embodiments, as shown in FIG. 21, heart valve deployment system 510 may comprise a split primary capsule 532 wherein the primary capsule is divided into multiple portions, for example, a proximal portion 532a and a distal portion 532b that are moveable axially relative to each other, and relative to valve support tube assembly 536 carrying or supporting a prosthetic heart valve 520 thereon. The distal and proximal primary capsule portions may be brought together in order to enclose therewithin the prosthetic heart valve 520. FIG. 22 illustrates the heart valve deployment system 510 in a partially deployed state or configuration. Tube assembly 539 comprises the proximal primary capsule portion 532a at its distal end. The proximal primary capsule portion 532a is slidably disposed over a proximal portion of secondary capsule 534. Movement of the proximal end of the tube assembly 539 may be directly transferred to the proximal primary capsule portion 532a and causes a corresponding movement of the proximal primary capsule portion 532a. For example, proximal movement of the proximal end of the tube assembly 539 is directly transferred to the proximal primary capsule portion 532a and causes a corresponding proximal movement of the proximal primary capsule portion 532a. Likewise, distal movement of the proximal end of the tube assembly 539 is directly transferred to the proximal primary capsule portion 532a and causes a corresponding distal movement of the proximal primary capsule portion 532a. In some embodiments, the tube assembly 539 is further configured to transmit a rotational force or movement onto the proximal primary capsule portion 532a. Primary capsule 532 is shown in FIG. 22 in a retracted state in that the proximal primary capsule portion 532a has been moved proximally to uncover a first portion of the secondary capsule 534 and the distal primary capsule portion 532b has been moved distally to uncover a second portion of the secondary capsule 534 to thereby allow prosthetic heart valve 520 to partially expand within the secondary capsule 534. Tube assembly 540 comprises the distal primary capsule portion 532b at a distal end region of tube assembly 540. Tube assembly 540 is slidably disposed within a lumen of tube assembly 536. The distal primary capsule portion 532b is slidably disposed over a distal portion of secondary capsule 534. Movement of the proximal end of the tube assembly 540 may be directly transferred to the distal primary capsule portion 532b and causes a corresponding movement of the distal primary capsule portion 532*b*. For example, proximal movement of the distal end of the tube assembly 540 is directly transferred to the distal primary capsule portion 532*b* and causes a corresponding proximal movement of the distal primary capsule portion 532*b*. Likewise, distal movement of the proximal end of the tube assembly 540 is directly transferred to the distal primary capsule portion 532*b* and causes a corresponding distal movement of the distal primary capsule portion 532*b*. In some embodiments, the tube assembly 540 is further configured to transmit a rotational force or movement onto the distal primary capsule portion 532*b*. In some embodiments, tube assembly 540 may comprise one or more lumens, for example to pass a guidewire therethrough.

Figure 23:
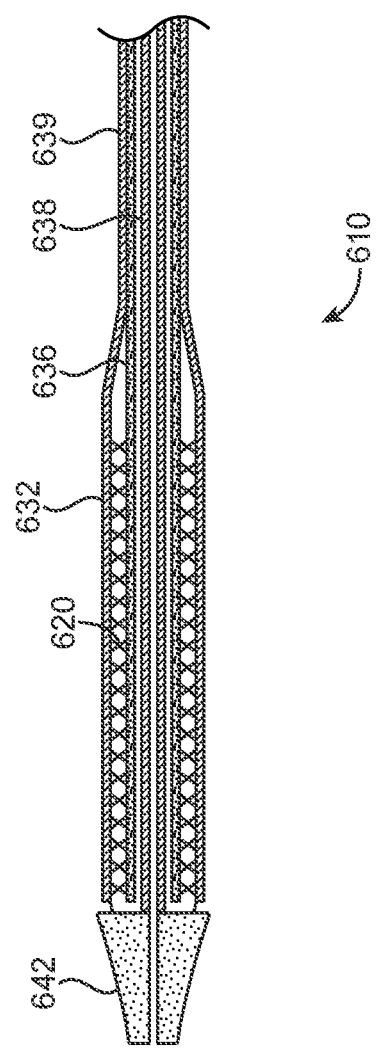
FIG. 23 is a side view of another alternative embodiment of the prosthetic heart valve stepped deployment system in a loaded state.
Figure 24:
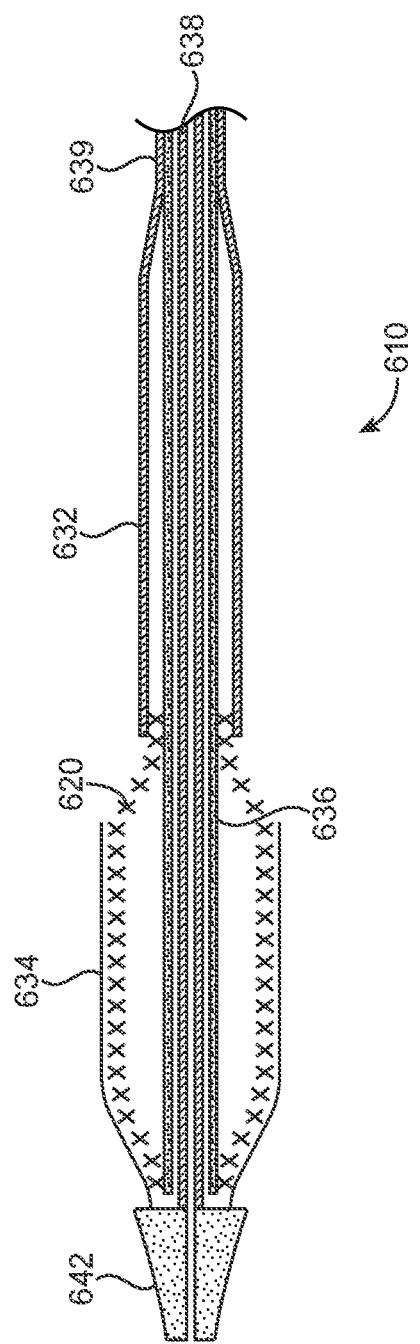
FIG. 24 is a side view of the prosthetic heart valve stepped deployment system of FIG. 23 in a partially deployed state.
Figure 25:
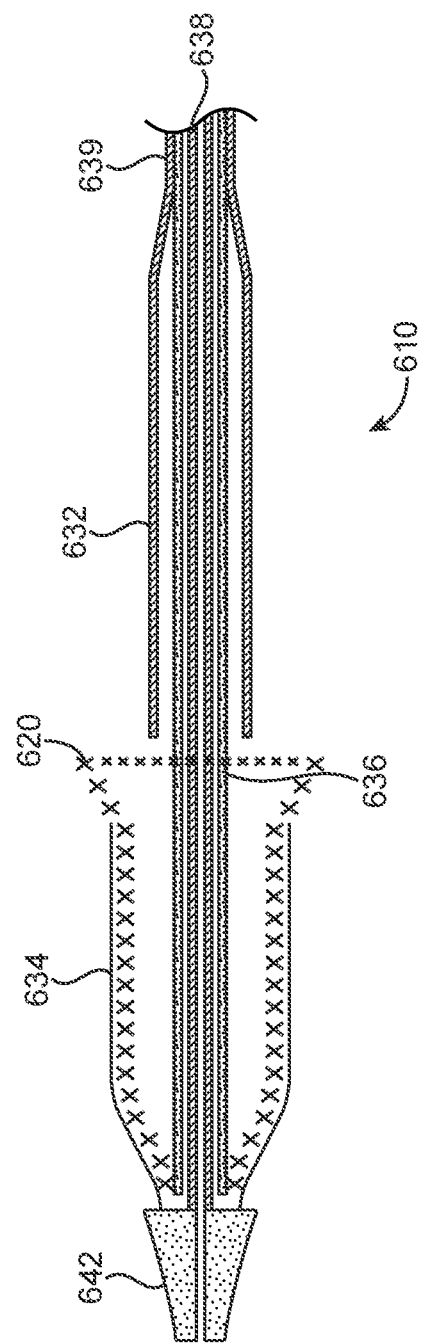
FIG. 25 is a side view of the prosthetic heart valve stepped deployment system of FIG. 23 in a partially deployed state.

Another embodiment of the prosthetic heart valve deployment system 610 is illustrated in FIGS. 23-25. FIG. 23 illustrates heart valve deployment system 610 in a loaded state or configuration. In some embodiments, as shown in FIG. 23, heart valve deployment system 610 may comprise a tube assembly 639 comprising a primary capsule 632 at its distal end. Tube assembly 639 is slidably disposed over valve supporting tube assembly 636 wherein tube assembly 636 resides within a lumen of tube assembly 639. Tube assembly 639 can move relative to tube assembly 636. The primary capsule 632 is slidably disposed over the secondary capsule 634. Movement of the proximal end of the tube assembly 639 may be directly transferred to the primary capsule 632 and causes a corresponding movement of the primary capsule 632. For example, proximal movement of the proximal end of the tube assembly 639 is directly transferred to the primary capsule 632 and causes a corresponding proximal movement of the primary capsule 632. Likewise, distal movement of the proximal end of the tube assembly 639 is directly transferred to the primary capsule 632 and causes a corresponding distal movement of the primary capsule 632. In some embodiments, the tube assembly 639 is further configured to transmit a rotational force or movement onto the primary capsule 632.

In some embodiments, as illustrated in FIGS. 23-25, tube assembly 636 is slidably disposed over tube assembly 638 wherein tube assembly 638 resides within a lumen of tube assembly 636. Tube assembly 638 can move relative to tube assembly 636. Tube assembly 638 comprises at its distal end a tapered nose piece 642 and a secondary capsule 634. Movement of the proximal end of the tube assembly 638 may be directly transferred to the nose piece 642 and the secondary capsule 634 and causes a corresponding movement of both the nose piece 642 and the secondary capsule 634. For example, proximal movement of the proximal end of the tube assembly 638 is directly transferred to both the nose piece 642 and the secondary capsule 634 and causes a corresponding proximal movement of both the nose piece 642 and the secondary capsule 634. Likewise, distal movement of the proximal end of the tube assembly 638 is directly transferred to both the nose piece 642 and the secondary capsule 634 and causes a corresponding distal movement of both the nose piece 642 and the secondary capsule 634. In some embodiments, the tube assembly 638 is further configured to transmit a rotational force or movement onto both the nose piece 642 and the secondary capsule 634. In some embodiments, the tapered nose piece 642 mounted at the distal end of tube assembly 638 allows the delivery or deployment system to easily pass through the native vascular system and to easily cross the native valve atraumatically In certain embodiments, nose piece 642 may comprise a lumen, e.g., for passing a guidewire therethrough. Tube assemblies 636, 638, and 639 extend distally from a stepped deployment system handle. One or more portions of the tube assemblies may be formed as a braided tube. For example, one or more portions of the tube assemblies may be a thermoplastic elastomer, such as Pebax®, with an embedded braided metal layer constructed from stainless steel wire. Other configurations are also acceptable, with the tube assemblies serving to help deploy a valve prosthesis in a stepwise deployment procedure. In some embodiments, the tube assemblies are constructed to be sufficiently flexible for passage through a patient's vasculature yet exhibit sufficient longitudinal rigidity to effectuate desired axial movement of the tube assemblies. In some embodiments, the tube assemblies are constructed to be sufficiently rigid for direct delivery procedures such as transapical or transaortic procedures.

FIG. 24 illustrates the heart valve deployment system 610 in a partially deployed state or configuration wherein the primary capsule 632 has been partially retracted in a proximal direction thereby uncovering the secondary capsule 634 and partially uncovering prosthetic valve 620. Prosthetic valve 620 is shown partially expanded within the secondary capsule 634 in FIG. 24. In some embodiments, as shown in FIGS. 24 and 25, the secondary capsule 634 may be configured so that movement of the secondary capsule 634 in a proximal direction covers prosthetic valve 620 and movement of the secondary capsule in a distal direction uncovers prosthetic valve 620. In some embodiments, as shown in FIGS. 23-25, the secondary capsule may only cover or contain one or more portions of a prosthetic valve for delivery. In FIG. 25, the primary capsule has been fully retracted in a proximal direction to fully uncover prosthetic valve 620. A first portion of prosthetic valve 620 is shown partially expanded within the secondary capsule 634 and a second portion of prosthetic valve 620 is shown fully expanded or deployed in FIG. 25.

In some embodiments, the heart valve deployment system may comprise a split primary capsule wherein the primary capsule is divided into multiple portions, for example, a proximal portion and a distal portion that are moveable axially relative to each other, and relative to valve support tube assembly carrying, supporting, and/or retaining a prosthetic heart valve thereon. The distal and proximal primary capsule portions may be brought together in order to enclose therewithin a prosthetic heart valve. In some embodiments, the heart valve deployment system may comprise a split secondary capsule wherein the secondary capsule is divided into multiple portions, for example, a proximal portion and a distal portion that are moveable axially relative to each other, and relative to valve support tube assembly carrying, supporting, and/or retaining a prosthetic heart valve thereon. The distal and proximal secondary capsule portions may be brought together in order to enclose therewithin a prosthetic heart valve.

In some embodiments, the heart valve deployment system may comprise a primary capsule that is retracted or moved axially in a proximal direction to uncover or move off of a prosthetic valve. In some embodiments, the heart valve deployment system may comprise a primary capsule that is retracted or moved axially in a distal direction to uncover or move off of a prosthetic valve. In some embodiments, the heart valve deployment system may comprise a secondary capsule that is retracted or moved axially in a proximal direction to uncover or move off of a prosthetic valve. In some embodiments, the heart valve deployment system may comprise a secondary capsule that is retracted or moved axially in a distal direction to uncover or move off of a prosthetic valve.

In some embodiments, the heart valve deployment system may comprise a primary capsule and a secondary capsule that are both retracted or moved axially in a proximal direction to uncover or move off of a prosthetic valve. In some embodiments, the heart valve deployment system may comprise a primary capsule and a secondary capsule that are both retracted or moved axially in a distal direction to uncover or move off of a prosthetic valve. In some embodiments, the heart valve deployment system may comprise a primary capsule that is retracted or moved axially in a proximal direction to uncover or move off of a prosthetic valve and a secondary capsule that is retracted or moved axially in a distal direction to uncover or move off of a prosthetic valve. In some embodiments, the heart valve deployment system may comprise a primary capsule that is retracted or moved axially in a distal direction to uncover or move off of a prosthetic valve and a secondary capsule that is retracted or moved axially in a proximal direction to uncover or move off of a prosthetic valve.

In some embodiments, the heart valve deployment system may comprise a primary capsule that covers one or more portions of a prosthetic valve. In some embodiments, the heart valve deployment system may comprise a secondary capsule that covers one or more portions of a prosthetic valve. In some embodiments, the heart valve deployment system may comprise more than two capsules for delivering a prosthetic valve in a multi-stepped deployment procedure.

The type of prosthetic heart valve to be delivered and the method of delivery will help guide the design and configuration of the heart valve deployment system. For example, the transapical delivery of a prosthetic mitral valve comprising support arms may require a heart valve deployment system that is configured differently than a heart valve deployment system that is configured for transfemoral delivery of a prosthetic aortic valve that does not have support arms.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed:

1. A system for replacing a heart valve of a patient, the system comprising:
   a delivery device comprising:
   a first tube assembly comprising a nose piece coupled to a distal end of a distal end portion of the first tube assembly;
   a primary capsule configured to be disposed over the distal end portion of the first tube assembly in a loaded state of the delivery device; and
   a secondary capsule comprising a distal portion and a proximal portion, wherein the secondary capsule is configured to be disposed within the primary capsule and further disposed over the distal end portion of the first tube assembly in the loaded state, and further wherein a distal end portion of the distal portion of the secondary capsule is coupled to the nose piece.

2. The system of claim 1, wherein the primary capsule is configured to translate relative to the secondary capsule.

3. The system of claim 1, further comprising a second tube assembly disposed around the first tube assembly, and wherein the second tube assembly is configured to support a prosthetic heart valve.

4. The system of claim 3, further comprising the prosthetic heart valve comprising a stent frame and a valve structure coupled to the stent frame, wherein the prosthetic heart valve is configured to circumscribe at least a portion of the second tube assembly while being compressively retained within the secondary capsule and the primary capsule in the loaded state.

5. The system of claim 3, wherein the secondary capsule is further configured to translate relative to the second tube assembly.

6. The system of claim 1, wherein the primary capsule is configured to be proximally retracted relative to the secondary capsule to a partially deployed state of the delivery device, wherein the partially deployed state comprises at least a portion of the secondary capsule radially expanded outside a distal end of the primary capsule.

7. The system of claim 6, wherein the partially deployed state further comprises at least the proximal portion of the secondary capsule radially expanded outside the distal end of the primary capsule.

8. The system of claim 6, wherein the secondary capsule is configured to be distally advanced relative to the primary capsule from the partially deployed state of the delivery device to a fully deployed state of the delivery device.

9. The system of claim 6, further comprising an expandable stent frame comprising a proximal portion and a distal portion, wherein the partially deployed state of the delivery device further comprises a proximal portion of the expandable stent frame radially expanded outside of the primary capsule and the secondary capsule.

10. The system of claim 6, further comprising an expandable stent frame comprising a proximal portion and a distal portion, wherein the partially deployed state of the delivery device further comprises a distal portion of the expandable stent frame in a collapsed state within the primary capsule.

11. The system of claim 1, wherein the primary capsule comprises a circumferential rigidity that is greater than a circumferential rigidity of the secondary capsule.

* * * * *